US008606355B1

(12) United States Patent
Krause

(10) Patent No.: US 8,606,355 B1
(45) Date of Patent: Dec. 10, 2013

(54) THERAPY SYSTEM INCLUDING CARDIAC RHYTHM THERAPY AND NEUROSTIMULATION CAPABILITIES

(75) Inventor: Paul G. Krause, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 82 days.

(21) Appl. No.: 13/016,792

(22) Filed: Jan. 28, 2011

Related U.S. Application Data

(60) Provisional application No. 61/299,816, filed on Jan. 29, 2010.

(51) Int. Cl.
*A61N 1/00* (2006.01)

(52) U.S. Cl.
USPC ............................................................ 607/9

(58) Field of Classification Search
USPC ...................... 607/9, 2, 5, 7, 17, 44
See application file for complete search history.

(56) References Cited

U.S. PATENT DOCUMENTS

| 4,374,382 | A | 2/1983 | Markowitz |
| 5,117,824 | A | 6/1992 | Keimel et al. |
| 5,545,186 | A | 8/1996 | Olson et al. |
| 5,755,736 | A | 5/1998 | Gillberg et al. |
| 6,006,134 | A | 12/1999 | Hill et al. |
| 2006/0116737 | A1 * | 6/2006 | Libbus .......................... 607/44 |
| 2006/0241697 | A1 * | 10/2006 | Libbus et al. .................... 607/2 |

* cited by examiner

*Primary Examiner* — George Manuel
*Assistant Examiner* — Robert N Wieland
(74) *Attorney, Agent, or Firm* — Carol F. Barry

(57) ABSTRACT

An implantable medical system is disclosed that is configured to detect a laryngeal activation response of a patient to an electrical stimulation signal. Detection of the laryngeal activation can be used to control vagal stimulation therapy to a patient.

17 Claims, 14 Drawing Sheets

US 8,606,355 B1

THERAPY SYSTEM INCLUDING CARDIAC RHYTHM THERAPY AND NEUROSTIMULATION CAPABILITIES

CROSS-REFERENCE

This application claims the benefit of U.S. Provisional Patent Application No. 61/299,816, filed on Jan. 29, 2010. The disclosure of the above application is incorporated herein by reference in its entirety.

TECHNICAL FIELD

The disclosure relates to medical devices and, more particularly, to medical devices that deliver electrical stimulation therapy.

BACKGROUND

Vagal nerve stimulation can result in reduction of heart rate and potentially change blood pressure, as noted in U.S. Pat. No. 6,006,134 to Hill et al. issued Dec. 21, 1999, and assigned to the assignee of the present invention, the disclosure of which is incorporated by reference in its entirety herein. Depending upon the proximity of vagal nerve stimulation to the larynx, one prominent side-effect can be laryngeal activation. While a medical device is being implanted into a patient, the patient is typically anesthetized and, therefore, unable to indicate when laryngeal activation is occurring. Physicians generally need to observe laryngeal activation to adjust the delivery of the electrical stimulation.

After the medical device has been implanted and the patient is ambulatory, laryngeal activation can still occur due to, for example, postural changes or lead migration. Laryngeal activation is uncomfortable for a patient. It is therefore desirable to address potential laryngeal activation.

DETAILED DESCRIPTION

Figure 1:
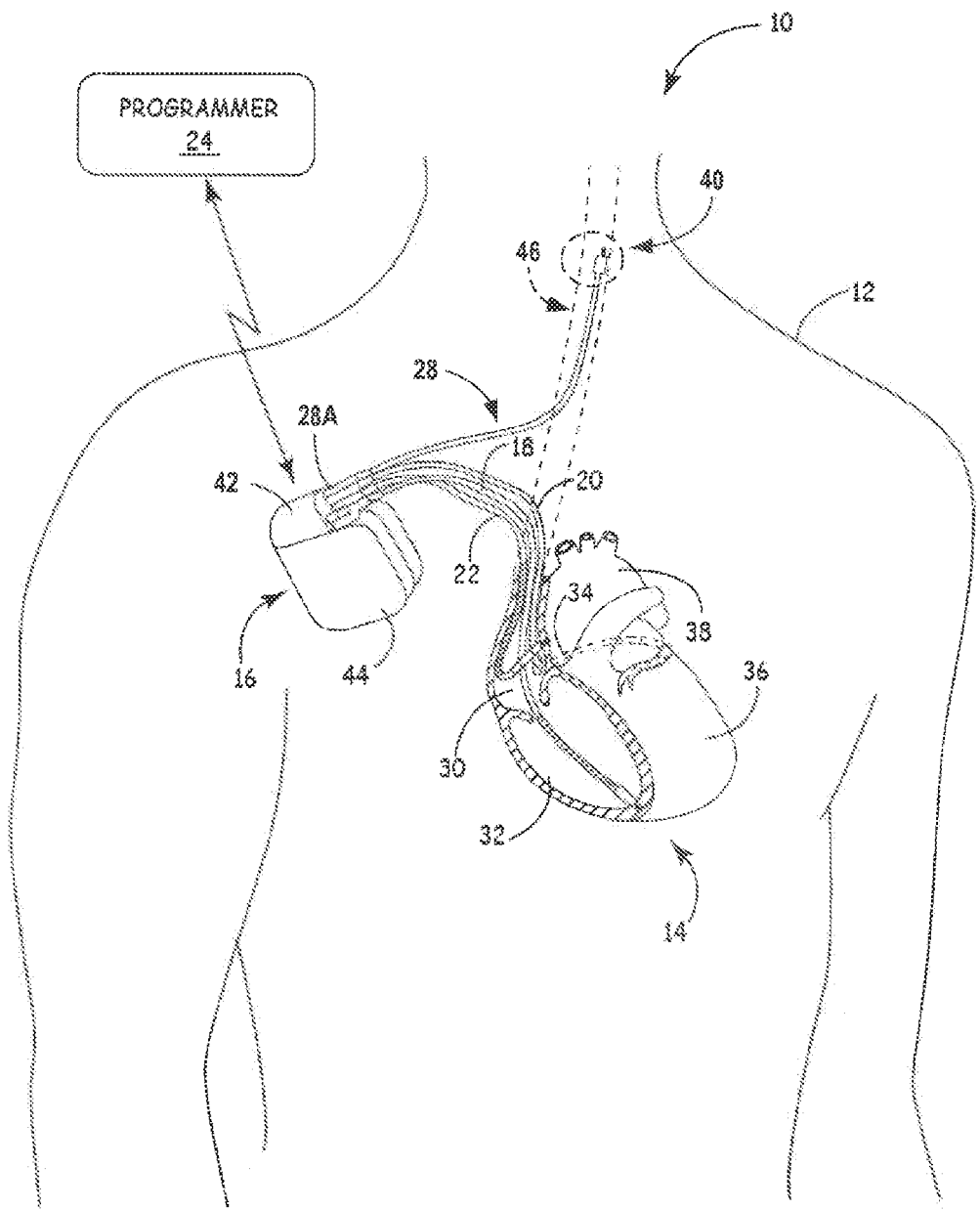
FIG. 1 is a conceptual diagram illustrating an exemplary therapy system including an implantable medical device (IMD) that delivers cardiac and neurostimulation therapy to a patient.

The disclosure is directed toward features of a therapy system that includes a cardiac therapy module and a neurostimulation therapy module, where the features may help detect whether an implanted medical lead electrically coupled to the neurostimulation module has caused larynx activation. The cardiac therapy module and a neurostimulation therapy module may be enclosed in separate housings (e.g., as part of different medical devices) or in a common medical device housing. The cardiac therapy module may provide cardiac rhythm therapy to a heart of a patient, e.g., pacing, cardioversion, and/or defibrillation therapy via one or more electrodes. The electrodes may be intravascular or extravascular. An extravascular tissue site may be outside of the patient's heart, and outside of arteries, veins, or other vasculature of the patient. The neurostimulation therapy module may deliver electrical stimulation signals to a tissue site via electrodes electrically connected to the neurostimulation therapy module. The neurostimulation may help modulate an autonomic nervous system of the patient or improve vascular tone of the patient. The electrodes electrically connected to the neurostimulation therapy module may be intravascular or extravascular.

In some examples, the tissue site for the neurostimulation therapy may include at least one of a nonmyocardial tissue site or a nonvascular cardiac tissue site. A nonmyocardial tissue site may include a tissue site that does not include cardiac muscle (e.g., the myocardium). For example, a nonmyocardial tissue site may be proximate a muscle other than cardiac muscle, an organ other than the heart, or neural tissue. A tissue site proximate a nerve may be a neural tissue site to which delivery of electrical stimulation may activate the nerve. In some examples, a tissue site proximate a nerve may be in a range of about zero centimeters to about ten centimeters from the nerve, although other distance ranges are contemplated and may depend upon the nerve. The nonmyocardial tissue site may include extravascular tissue sites or intravascular tissue sites. A nonvascular cardiac tissue site may include, for example, a cardiac fat pad.

The target neurostimulation site to which the neurostimulation therapy module delivers electrical stimulation may be a sufficient distance from the heart, such that the delivery of neurostimulation therapy to the patient via neurostimulation electrodes electrically connected to the neurostimulation module does not capture (e.g., evoke a cardiac contraction) the heart or otherwise affect the rhythm of the heart. The neurostimulation lead may change position over time, e.g., migrate from the implant site. In some cases, this may cause the neurostimulation electrodes to migrate towards the heart of the patient. For example, the neurostimulation lead may be implanted intravascularly, e.g., within the jugular vein, and proximate to a target stimulation site, such as the vagus nerve. Over time, the neurostimulation electrodes may migrate from the implant site, e.g., through the jugular vein, toward the heart of the patient or closer to the larynx.

Post-implant migration of leads or patient posture changes may alter the initial relative positioning of the neurostimulation lead relative to the heart. The initial relative positioning of the neurostimulation lead relative to the heart may take place when the neurostimulation lead is implanted within the patient. It may be undesirable for the neurostimulation therapy module to deliver the neurostimulation therapy to the heart of the patient because the delivery of neurostimulation to the heart may capture the heart, which is not the intended target for the neurostimulation. It may also be undesirable to deliver neurostimulation to the patient when the neurostimulation lead migrates from the intended implant site because the neurostimulation may affect the detection of cardiac signals by the cardiac therapy module (e.g., sensing of the neurostimulation signals by the cardiac therapy module).

In accordance with various examples of this disclosure, a therapy system may automatically withhold neurostimulation therapy, e.g., prevents the neurostimulation therapy module from delivering electrical stimulation to the patient via the neurostimulation electrodes, when the therapy system detects that the neurostimulation lead has migrated a certain distance away from the implant site, or otherwise changed position. Some of the features described herein include techniques for determining whether one or more electrodes of the neurostimulation lead have migrated toward the heart and withholding the delivery of neurostimulation via the migrated lead if an undesirable amount of lead movement is detected.

In some examples, an implantable medical device (IMD) that includes at least one of the neurostimulation therapy module or the cardiac therapy module may determine whether neurostimulation electrodes of a neurostimulation lead have migrated toward the heart by delivering an electrical stimulation signal via the neurostimulation lead and analyzing a physiological signal to detect the patient's physiological response to the delivered neurostimulation signal. The physiological response may be, for example, a response by the patient's heart or a nerve. A characteristic of the physiological response may indicate that the neurostimulation electrodes of a neurostimulation lead have not migrated from the target tissue site, such that the possibility that delivery of neurostimulation therapy to the patient via the neurostimulation electrodes capture the patient's heart is reduced.

In another example, the IMD may determine whether neurostimulation electrodes of a neurostimulation lead have migrated towards the patient's heart based on a cardiac signal, e.g., an electrocardiogram (ECG) or electrogram (EGM) signal, sensed by the neurostimulation electrodes. A signal parameter of the sensed cardiac signal, such as an amplitude, a polarity, a frequency, or morphology of the signal, may indicate whether the neurostimulation electrodes have migrated toward the patient's heart, and, as a result, whether the withholding or other adjustment to the delivery of neurostimulation therapy is desirable.

In some examples, the IMD may also compare or correlate the cardiac signals (e.g., ECG or EGM) sensed on via the neurostimulation electrodes, referred to as a far field cardiac signal, to a near field cardiac signal, which includes a cardiac signal sensed via the cardiac therapy electrodes electrically connected to the cardiac therapy module. If a characteristic of the near field cardiac signal is within a threshold range of a characteristic of the far field cardiac signal, the IMD may determine that the neurostimulation electrodes have migrated toward the patient's heart and that the withholding of neurostimulation therapy is desirable.

The IMD may also utilize one or more other techniques in addition or instead of the examples features for detecting movement of a neurostimulation lead described above. For example, the IMD may monitor an impedance of an electrical path between the neurostimulation electrodes and one or more of the cardiac electrodes to detect migration of the neurostimulation lead. The IMD may use various modalities to determine the impedance between the neurostimulation and cardiac leads. The IMD may compare the determined impedance value to a threshold value and selectively withhold therapy delivery by the neurostimulation module based on the comparison.

While techniques for minimizing the possibility that a neurostimulation therapy module may deliver neurostimulation that captures of a heart of a patient are described herein with respect to an IMD that comprises a cardiac therapy module and a neurostimulation therapy in a common outer housing, in other examples, the techniques described herein are also applicable to a therapy system that includes two IMDs, where a first IMD includes the cardiac therapy module and a second IMD includes the neurostimulation therapy module. The first and second IMDs may have physically separate outer housings that are separately implanted within the patient.

FIG. 1 is a conceptual diagram illustrating an example therapy system 10 that provides cardiac rhythm management therapy and neurostimulation therapy to patient 12. Therapy system 10 includes implantable medical device (IMD) 16, which is connected (or "coupled") to leads 18, 20, 22, 28, and programmer 24. IMD 16 may be subcutaneously or submuscularly implanted in the body of a patient 12 (e.g., in a chest cavity, lower back, lower abdomen, or buttocks of patient 12).

Figure 4:
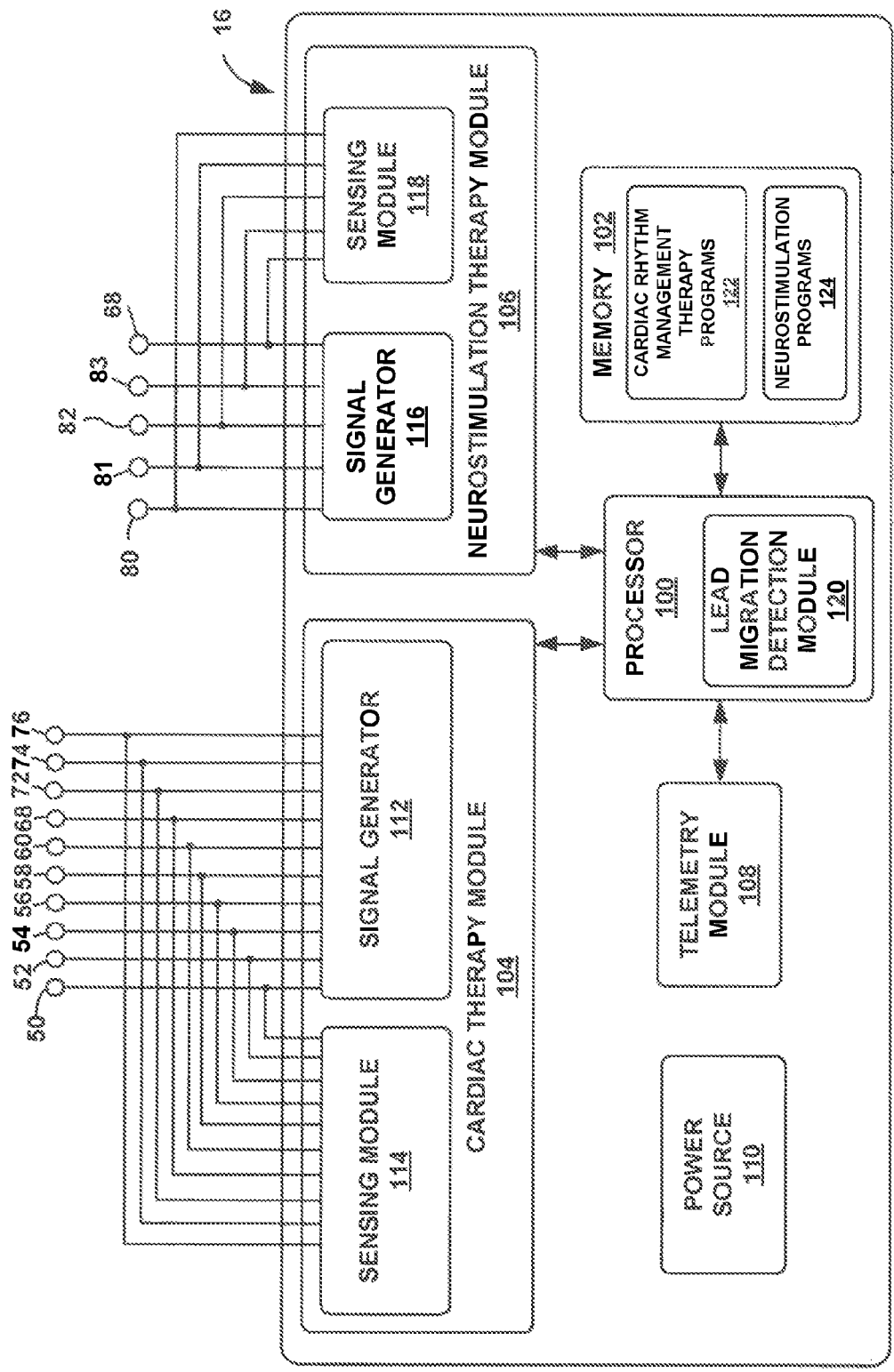
FIG. 4 is a functional block diagram of the IMD of FIG. 1, which includes a lead migration detection module.

As described in further detail with respect to FIG. 4, IMD 16 may include a cardiac therapy module (not shown in FIG. 1) and a neurostimulation module (not shown in FIG. 1) enclosed within outer housing 44. The cardiac therapy module may generate and deliver cardiac rhythm management therapy to heart 14 of patient 12, and may include, for example, an implantable pacemaker, cardioverter, and/or defibrillator that provide therapy to heart 14 of patient 12 via electrodes coupled to one or more of leads 18, 20, and 22. In some examples, the cardiac therapy module may deliver pacing pulses, but not cardioversion or defibrillation pulses, while in other examples, the cardiac therapy module may deliver cardioversion or defibrillation pulses, but not pacing pulses. In addition, in further examples, cardiac therapy module may deliver pacing, cardioversion, and defibrillation pulses. IMD 16 may deliver pacing that includes one or both of anti-tachycardia pacing (ATP) and cardiac resynchronization therapy (CRT).

The neurostimulation module of IMD 16 may include a signal generator that generates and delivers electrical stimulation to a tissue site of patient 12, e.g., tissue proximate a vagus nerve, a spinal cord, or heart 14 of patient 12. As previously indicated, in some examples, the tissue site may include at least one of a nonmyocardial tissue site or a nonvascular cardiac tissue site. A nonmyocardial tissue site may include a tissue site that does not include cardiac muscle, e.g., the myocardium. For example, a nonmyocardial tissue site may be proximate a muscle other than cardiac muscle, an organ other than heart 14, or neural tissue. The nonmyocardial tissue site may include extravascular tissue sites or intravascular tissue sites. In the example shown in FIG. 1, electrodes of lead 28 are position to deliver electrical stimulation to target tissue site 40 (also referred to as "target stimulation site") proximate a vagus nerve of patient 12. The vagus nerve is primarily referred to herein as the target nerve for neurostimulation therapy. However, in other examples, the target nerve may be other nerves within patient 12, such as nerves branching from the vagus nerve, the spinal cord, and the like. A nonvascular cardiac tissue site can include, for example, cardiac fat pads.

In some examples, delivery of electrical stimulation to a tissue site proximate a nerve or a nonmyocardial tissue site that may not be proximate a nerve may help modulate an autonomic nervous system of patient 12. In some examples, IMD 16 may deliver electrical stimulation therapy to a nerve of patient 12 via a lead implanted within vasculature (e.g., a blood vessel) of patient 12. In some examples, IMD 16 may deliver electrical stimulation that is delivered to peripheral nerves that innervate heart 14, or fat pads on heart 14 that may contain nerve bundles. Stimulation may be delivered to extravascular tissue sites, for example, when lead 28 is not implanted within vasculature, such as within a vein, artery or heart 14. In other examples, stimulation may be delivered to a nonmyocardial tissue site via electrodes of an intravascular lead that is implanted within vasculature.

In some examples, delivery of electrical stimulation to a nonmyocardial tissue site may provide cardiac benefits to patient 12. For example, delivery of electrical stimulation to a nonmyocardial tissue site by IMD 16 may help treat heart failure. In addition, in some examples, the delivery of electrical stimulation by IMD 16 may help modulate an autonomic nervous system of patient 12. Delivery of electrical stimulation to a nerve of patient 12 to may help reduce or eliminate cardiovascular conditions such as bradycardia, tachycardia, unhealthy cardiac contractions, ischemia, inefficient heart pumping, inefficient collateral circulation of heart 14 or cardiac muscle trauma. In addition, delivery of electrical stimulation may complement antitachycardia pacing or provide back-up therapy to cardiac therapy delivered by IMD 16.

In the example shown in FIG. 1, the neurostimulation therapy module of IMD 16 delivers electrical stimulation therapy to a nerve of patient 12 via a lead implanted within vasculature (e.g., a blood vessel) of patient 12. In particular, lead 28 is implanted such that electrodes of lead 28 are positioned within jugular vein 46 and proximate the vagus nerve (not shown). In other examples, IMD 16 may provide electrical stimulation therapy to a parasympathetic nerve of patient 12 other than the vagus nerve. Stimulation of a parasympathetic nerve of patient 12 may help slow intrinsic rhythms of heart 14, which may complement antitachyarrhythmia therapy (e.g., antitachycardia pacing, cardioversion or defibrillation) delivered by IMD 16. In this way, neurostimulation therapy may help control a heart rate of patient 12 or otherwise influence cardiac function.

In other examples, electrodes of lead 28 may be positioned to deliver electrical stimulation to any other suitable nerve (e.g., a peripheral nerve), spinal cord, organ, muscle or muscle group in patient 12, which may be selected based on, for example, a therapy program selected for a particular patient. In some examples, the neurostimulation module of IMD 16 may deliver electrical stimulation to other sympathetic or parasympathetic nerves, baroreceptors, the carotid sinus or a cardiac branch of the vagal trunk of patient 12 in order to facilitate the delivery of therapy by the cardiac therapy module of IMD 16.

In FIG. 1, leads 18, 20, and 22 extend into the heart 14 of patient 12 to sense electrical activity (electrical cardiac signals) of heart 14 and/or deliver electrical stimulation (cardiac therapy) to heart 14. In particular, right ventricular (RV) lead 18 extends through one or more veins (not shown), superior vena cava (not shown), and right atrium 30, and into right ventricle 32. Left ventricular (LV) coronary sinus lead 20 extends through one or more veins, the vena cava, right atrium 30, and into coronary sinus 34 to a region adjacent to the free wall of left ventricle 36 of heart 14. Right atrial (RA) lead 22 extends through one or more veins and the vena cava, and into right atrium 30 of heart 14. In other examples, IMD 16 and, more particularly, the cardiac therapy module of IMD 16, may deliver stimulation therapy to heart 14 by delivering stimulation, via the cardiac therapy module, to an extravascular tissue site in addition to or instead of delivering stimulation via electrodes of intravascular leads 18, 20, 22. In such examples, therapy system 10 includes one or more extravascular leads mechanically and electrically connected to IMD 16.

The cardiac therapy module may sense electrical signals attendant to the depolarization and repolarization of heart 14 via electrodes (not shown in FIG. 1) coupled to at least one of the leads 18, 20, 22. These electrical signals within heart 14 may also be referred to as cardiac signals or electrical cardiac signals. In some examples, the cardiac therapy module provides pacing pulses to heart 14 based on the electrical cardiac signals sensed within heart 14. The configurations of electrodes used by the cardiac therapy module for sensing and pacing may be unipolar or bipolar. The cardiac therapy module may also provide defibrillation therapy and/or cardioversion therapy via electrodes located on at least one of the leads 18, 20, 22 and one or more electrodes on housing 44 of IMD 16. IMD 16 may detect arrhythmia of heart 14, such as fibrillation of ventricles 32 and 36, and deliver defibrillation therapy to heart 14 in the form of electrical pulses via one or more of leads 18, 20, and 22. In some examples, the cardiac therapy module may be programmed to deliver a progression of therapies, e.g., pulses with increasing energy levels, until a fibrillation of heart 14 is stopped. IMD 16 detects fibrillation employing one or more fibrillation detection techniques known in the art.

The neurostimulation therapy module of IMD 16 may provide a programmable stimulation signal (e.g., in the form of electrical pulses or a continuous signal) that is delivered to target tissue site 40 by implantable medical lead 28, and more particularly, via one or more stimulation electrodes carried by lead 28. Proximal end 28A of lead 28 may be both electrically and mechanically coupled to connector 42 of IMD 16 either directly or indirectly (e.g., via a lead extension). In particular, conductors disposed in the lead body of lead 28 may electrically connect stimulation electrodes (and sense electrodes, if present) of lead 28 to IMD 16. In some examples, the neurostimulation therapy module of IMD 16 may be electrically coupled to more than one lead directly or indirectly (e.g., via a lead extension).

In the example of FIG. 1, one or more electrodes of lead 28 are intravascularly implanted in patient 12 proximate to target tissue stimulation site 40, i.e., proximate to a vagus nerve (not shown). In particular, one or more neurostimulation electrodes of lead 28 are implanted within jugular vein 46. Lead 28 may be inserted into the jugular vein 46 using a technique similar to that used for implanting leads 18, 20, and 22. Implanting lead 28 near the vagus nerve of patient 12 may be useful for delivering neurostimulation therapy to the vagus nerve without requiring lead 28 to be subcutaneously implanted in patient 12. Implantation lead 28 within jugular vein 46 may be useful for reducing trauma to patient 12, e.g., because lead 28 is not tunneled through subcutaneous tissue from IMD 16 to target tissue site 40.

The distal portion of lead 28 may include one or more electrodes (not shown) for delivering neurostimulation to target tissue site 40. Various electrode configurations of lead 28 are described in further detail with respect to FIGS. 2 and 3. In some examples, lead 28 may also carry sense electrodes (not shown) to permit IMD 16 to sense electrical signals, such as electrical cardiac signals or electrical nerve signals from the vagus nerve or spinal cord. Like the cardiac therapy module of IMD 16, in some examples, the neurostimulation module may deliver stimulation based on the electrical cardiac signals, which may be sensed by leads 18, 20, and 22. In some examples, described in greater detail below, the neurostimulation module may also deliver stimulation based on electrical cardiac signals sensed via lead 28.

In some examples, like the cardiac therapy module, the neurostimulation module of IMD 16 may also adjust and/or deliver therapy in response to a sensed cardiac event, e.g., depolarization or repolarization of heart 14, or an arrhythmia. For example, if the neurostimulation module delivers therapy to control heart rate, the sensed depolarization and repolarization of heart 14 may provide feedback for therapy adjustment. As another example, the neurostimulation module may deliver therapy to control heart rate in response to a sensed arrhythmia, which may include abnormal heart rhythms such as bradycardia, tachycardia or fibrillation. A sensing module of IMD 16 may detect an arrhythmia using any suitable technique, such as techniques that rely on detected electrical cardiac signals generated by the depolarization and repolarization of heart 14, heart rate, or hemodynamic parameters, such as blood oxygen levels, blood pressure, stroke volume, and the like.

In some cases, the delivery of neurostimulation by the neurostimulation module of IMD 16 may help eliminate or reduce the demands of pacing or defibrillation provided by the cardiac therapy module. This may help conserve the energy consumed by IMD 16 to manage the patient's cardiac condition. In other examples, the delivery of neurostimulation by the neurostimulation module of IMD 16 may help prevent or reduce the tendency of heart 14 to beat irregularly. Thus, in some examples, the neurostimulation module of IMD 16 may deliver therapy when the cardiac therapy module is not delivering therapy. This may help reduce the frequency with which the cardiac therapy module generates and delivers therapy to terminate an arrhythmia of heart 14.

In some examples, depending upon the target tissue site for the neurostimulation, the delivery of electrical stimulation by the neurostimulation module may also mitigate perceptible discomfort generated from the delivery of pacing pulses or cardioversion/defibrillation shocks by the cardiac therapy module. For example, if IMD 16 also delivers electrical stimulation to a spinal cord of patient 12, e.g., via an additional lead (not shown), the neurostimulation may produce paresthesia, which may help reduce the discomfort felt by patient 12 from the delivery of stimulation by the cardiac therapy module.

In general, the cardiac and neurostimulation modules of IMD 16 may deliver therapy at substantially the same time and/or at different times. For example, a processor within IMD 16 may control the cardiac and neurostimulation modules to deliver therapy substantially concurrently in response to detection of fibrillation. Additionally or alternatively, the neurostimulation module may provide neurostimulation prior to and/or subsequent to a defibrillation shock delivered by the cardiac therapy module. Other functions of therapy system 10, such as sensing electrical signals, may be performed coincident and/or in alternation with therapy delivery by the cardiac therapy module and/or neurostimulation module of IMD 16.

In some examples, the neurostimulation module may deliver neurostimulation therapy to patient 12 independently of the cardiac rhythm therapy delivered by the cardiac therapy module of IMD 16. For example, the neurostimulation module may be programmed to deliver neurostimulation to patient 12 according to a schedule that is determined independently of the actual delivery of cardiac therapy delivered by the cardiac therapy module. The schedule may be determined, for example, by a clinician based on a trial stimulation period in which multiple neurostimulation therapy schedules are tested on patient 12. The schedule may dictate when the neurostimulation module actively delivers electrical stimulation to patient 12 and when the neurostimulation module does not actively deliver electrical stimulation to patient 12.

In accordance with various examples of this disclosure, IMD 16 includes features for determining whether lead 28 has migrated from target tissue site 28 and/or towards heart 14. Although neurostimulation lead 28 is implanted proximate to target tissue site 40 and may include one or more fixation mechanisms that help secure the position of lead 28 within jugular vein 46, the position of lead 28 may change over time, e.g., migrate or drift from the implant site. Post-implant migration of lead 28 or changes in the posture of patient 12 may alter the position of lead 28 relative to heart 14. It may be desirable to determine whether lead 28 has migrated toward heart 14, e.g., determine whether the neurostimulation electrodes of lead 28 are within an particular distance of heart 14, because neurostimulation delivered by the neurostimulation electrodes of lead 28 may capture heart 14, or affect sensing of electrical cardiac signals by IMD 16. For example, the neurostimulation therapy module of IMD 16 may generate and deliver a relatively high frequency neurostimulation signal (e.g., about 50 Hertz (Hz)).

IMD 16 may utilize one or more techniques for determining whether lead 28 has migrated from the implant site or otherwise changed position relative to heart 14, the determination of which may be used to selectively withhold or suspend delivery of neurostimulation to patient 12 via lead 28.

In some example, IMD 16 may determine whether neurostimulation therapy to patient 12 should be withheld by delivering an electrical stimulation signal via one or more of the electrodes of lead 28, and analyzing a physiological signal to detect a response to the stimulation signal. In this way, the physiological signal may indicate a physiological response that indicates whether lead 28 has migrated from target tissue site 40. The physiological response may indicate whether lead 28 has migrated from target tissue site 40, in which case IMD 16 may adjust the delivery of neurostimulation to patient 12 (e.g., by suspending the delivery of neurostimulation or decreasing the intensity of neurostimulation). In this way, IMD 16 may selectively delivery neurostimulation therapy to patient 12 based on a sensed physiological response to the delivery of neurostimulation therapy.

In some examples, IMD 16 may analyze the physiological signal by analyzing an electrical muscle or nerve signal to detect a response to the stimulation signal. The characteristic of the electrical muscle or nerve signal that indicates the desired response to the delivery of the electrical stimulation signal by the neurostimulation therapy module of IMD 16 may be, for example, an amplitude or frequency of the electrical signal. The target characteristic of the electrical muscle or nerve signal may be determined by a clinician at any suitable time when lead 28 is known to be in the desired location within patient 12, e.g., immediately after lead 28 is implanted within patient 12.

The electrical muscle signal may be an electrical signal indicative of a movement of a muscle that may be activated by the neurostimulation, e.g., because the target nerve innervates the muscle. For example, in FIG. 1, following the delivery of a neurostimulation signal, IMD 16 may monitor an electrical signal indicative of the vibration of a laryngeal muscle. The movement of the muscle may be detected via en electromyogram (EMG) sensed via the sense electrodes of lead 28 or via an acoustic sensor, a pressure sensor, an accelerometer, or a piezoelectric sensor. The acoustic sensor, pressure sensor, accelerometer, or piezoelectric sensor may be located on a distal end of lead 28, located on a distal end of an additional lead (not shown) coupled to IMD 16, or located within the housing of IMD 16. Alternatively, the acoustic sensor, pressure sensor, accelerometer, or piezoelectric sensor may be a sensor implanted within patient 12 that communicates with IMD 16 and is physically separate from lead 28 and IMD 16.

IMD 16 may sense the electrical signal indicative of muscle movement (referred to herein as an "electrical muscle signal") to determine whether the stimulation signal is delivered to target tissue site 40 and a desirable distance from heart 14. A change in the muscle movement in response to the delivery of the neurostimulation signal may indicate that the coupling between the electrodes of lead 28 and the nerve innervating the muscle has changed, and, thus, lead 28 has migrated away from the target tissue site 40. For example, in the case of vagus nerve stimulation, a decrease in frequency of the vibration of the laryngeal muscle in response to the delivery of the neurostimulation signal may indicate that lead 28 has changed position relative to target tissue site 40. IMD 16 may, for example, compare the frequency of the sensed electrical muscle signal to a threshold value to determine whether lead 28 has moved.

The electrical nerve signal may be an electrical signal generated by a nerve, such as the target nerve for the neurostimulation therapy or a branch thereof, in response to an electrical stimulation signal delivered by the electrodes of lead 28. The response to the electrical stimulation signal may indicate, for example, whether the neurostimulation signal captured the nerve, and, therefore, is within a desired distance of the nerve. In the example shown in FIG. 1, the target nerve may be the vagus nerve, although other types of nerves are contemplated for the neurostimulation therapy. The electrical nerve signal may be sensed between two or more electrodes of lead 28. IMD 16 may analyze the electrical nerve signal for a response, for example, by measuring an amplitude of the electrical nerve signal and comparing the determined value to a threshold value. In this case, the electrical nerve signal may have a baseline amplitude value and a response to the stimulation signal may be characterized by a spike in amplitude. The nerve response may be characterized by an amplitude or other characteristics of a sensed electrical signal.

If IMD 16 does not detect an appropriate physiological response to the delivery of the stimulation signal, e.g., via the electrical muscle or nerve signal, then IMD 16 may withhold (e.g., suspend) the delivery of neurostimulation therapy to patient 12 or otherwise adjust the delivery of neurostimulation therapy (e.g., adjust the amplitude or frequency of the neurostimulation). An appropriate physiological response to the delivery of the stimulation signal may be characterized by a sensed electrical signal that has a particular signal characteristic, such as a particular amplitude. The signal characteristic may be determined by a clinician at any suitable time when lead 28 is known to be located at target tissue site 40, e.g., immediately after lead 28 is implanted within patient 12. IMD 16 may withhold the delivery of neurostimulation therapy to patient 12 because the absence of the appropriate physiological response detected via electrical muscle or nerve signal may indicate that the electrodes of neurostimulation lead 28 have migrated from target tissue site 40. That is, the sensed electrical nerve or muscle signal may indicate that the neurostimulation signal no longer generates a desired response at target tissue site 40. The absence of the appropriate physiological response to the delivery of the stimulation signal may be referred to as a loss of nerve capture. If IMD 16 detects nerve capture, e.g., via the appropriate physiological response to the neurostimulation signal, the IMD may continue to operate normally.

As another example, IMD 16 may deliver an electrical stimulation signal via one or more electrodes carried by lead 28 and analyze a sensed cardiac signal (e.g., an ECG or EGM signal) to detect a response to the stimulation signal. The ECG or EGM signal may be sensed via the neurostimulation electrodes electrically connected to the neurostimulation therapy module of IMD 16 via lead 28, or by the cardiac therapy electrodes electrically connected to the cardiac therapy module of IMD 16. In this example, IMD 16 may withhold delivery of neurostimulation therapy if a cardiac response to the neurostimulation therapy is detected via the sensed cardiac signal. The response may be referred to as an evoked response, which indicates cardiac capture. Cardiac capture may indicate that the neurostimulation signal stimulated heart 14. If IMD 16 does not detect cardiac capture in response to the delivery of a neurostimulation signal, IMD 16 may continue to operate normally. In this way, IMD 16 may selectively delivery neurostimulation therapy to patient 12 based on a sensed cardiac signal.

In other examples, IMD 16 may selectively withhold delivery of neurostimulation to patient 12 based on a cardiac signal, e.g., an ECG or EGM signal, sensed by the neurostimulation electrodes. The amplitude of the sensed cardiac signal may indicate whether the neurostimulation electrodes of lead 28 have migrated toward heart 14. In some examples, IMD 16 may compare an amplitude of the sensed ECG or EGM signal to a threshold value to determine whether the delivery of neurostimulation should be withheld. As the neurostimulation electrodes move closer to heart 14, the amplitude of an ECG or EGM signal sensed via the neurostimulation electrodes of lead 28 may change, e.g., increase or decrease, because of the proximity to heart 14. Thus, in some examples, IMD 16 may withhold the delivery of neurostimulation via the neurostimulation electrodes based on a comparison of the amplitude of the sensed ECG or EGM signal to a threshold value. In other examples, a polarity, morphology, or frequency content of an ECG or EGM signal may change dye to movement of lead 28 because the proximity of lead 28 relative to heart 14 may change. IMD 16 may selectively withhold delivery of neurostimulation based on the comparison of the polarity, morphology, or frequency content to a threshold value.

IMD 16 may also selectively withhold delivery of neurostimulation to patient 12 based on the presence or absence of one or both of a P-wave and an R-wave in an ECG or EGM signal sensed by lead 28. As one example, IMD 16 may analyze the ECG or EGM signal to determine the extent to which a P-wave or an R-wave are present in the sensed ECG or EGM signal. In this example, IMD 16 may determine the size of each of the P-wave and the R-wave, e.g., through integration or based on the amplitude, and compare the determined sizes of the R-wave and P-wave to each other. For example, IMD 16 may compare the size of the P-wave and the R-wave to determine a value that represents the size ratio between the R-wave and the P-wave. The size ratio between the R-wave and P-wave of a cardiac signal sensed via the electrodes of lead 28 may indicate whether lead 28 has migrated toward heart 14.

IMD 16 may control therapy, e.g., by selectively withholding delivery of neurostimulation, to patient 12 based on the comparison of the ratio value of the R-wave and P-wave sizes to a threshold value. When lead 28 is located at target tissue site 40, e.g., immediately after lead 28 is implanted in patient 12, the ratio of the P-wave to the R-wave may be determined and stored as a threshold value. IMD 16 may then determine a range of values centered around the determined value, and the range may be stored as a threshold range. If lead 28 migrated into right atrium 30 of heart 14, the ratio of the P-wave to the R-wave may be relatively large, e.g., greater than or equal to the threshold value and/or outside the threshold range, because the P-wave may be greater in size than the R-wave. If, however, lead 28 migrated into right ventricle 32, the ECG or EGM signal may include an R-wave, but not a P-wave or a relatively small P-wave. In this case, the ratio of the P-wave to the R-wave may be relatively small, e.g., less than or equal to the threshold value and/or outside the threshold range. Thus, IMD 16 may compare the determined ratio value to the range of values and selectively withhold delivery of neurostimulation to patient 12 based on the comparison of the ratio of the R-wave and P-wave sizes to a threshold value or threshold range.

In other examples, IMD 16 may determine a change in an amplitude, a polarity, a morphology, or frequency content of the ECG or EGM signal sensed via the neurostimulation electrodes of lead 28 over time and compare the determined value to a threshold value. A rate of change of the amplitude, polarity, morphology, or frequency content of the ECG or EGM signal over time may be used to track migration of the neurostimulation lead. For example, a sudden increase in the amplitude of the cardiac signal sensed via the neurostimulation electrodes may indicate the neurostimulation electrodes have migrated.

In some examples, IMD 16 may also compare or correlate the cardiac signals (e.g., ECG or EGM) sensed on via the neurostimulation electrodes of lead 28, referred to as a far field cardiac signal, to a near field cardiac signal, which includes a cardiac signal sensed via the cardiac therapy electrodes electrically connected to the cardiac therapy module via leads 18, 20, 22. Comparing the near and far field cardiac signals may include, for example, comparing an amplitude, a polarity, morphology, or frequency content of the signals to each other. For example, the relative difference in amplitudes of the near field and far field cardiac signals may indicate whether the neurostimulation electrodes have migrated toward heart 14, and whether the withholding of neurostimulation therapy is desirable. For example, if the amplitude of the near field cardiac signal is within a threshold range of the far field cardiac signal, IMD 16 may determine that the neurostimulation electrodes have migrated toward heart 14 and that the withholding of neurostimulation therapy is desirable.

Instead of or in addition to the comparison of amplitudes of the near field and far field cardiac signals, IMD 16 may correlate a portion of the near and far field cardiac signals to determine whether the electrodes of lead 28 have moved toward heart 14. A relatively high correlation between the near field and far field cardiac signals may indicate that electrodes of lead 28 may have migrated toward heart 14, such that withholding of neurostimulation therapy is desirable. The correlation that indicates a relatively high correlation may be selected by a clinician.

IMD 16 may also utilize one or more other techniques in addition or alternative to examples of features for detecting movement of electrodes of lead 28 described above. For example, IMD 16 may monitor an impedance of an electrical path between the neurostimulation electrodes of lead 28 and one or more of the cardiac electrodes of leads 18, 20, 22 to detect migration of neurostimulation lead 28. IMD 16 may use various modalities, e.g., a tripolar or a quadrapolar configuration, to determine the impedance of the electrical path between the neurostimulation and cardiac leads. IMD 16 may compare the determined impedance value to a threshold value and selectively withhold therapy delivery by the neurostimulation module based on the comparison.

As another example, IMD 16 may monitor a heart rate or heart rate variability of patient 12 to detect changes in the efficacy of neurostimulation. A decrease in the efficacy of neurostimulation may indicate that lead 28 has migrated from target tissue site 40. Accordingly, IMD 16 may withhold delivery of neurostimulation to patient 12 upon detecting a decrease in efficacy of neurostimulation.

In each of these examples, IMD 16 may transmit information to programmer 24 indicating that lead 28 has migrated from the implant site or otherwise changed position relative to heart 14, and/or neurostimulation therapy has been suspended in response to detecting the migration of lead 28. Upon receiving the information, programmer 24 may upload the received information to a remote server, from which a clinician may access the data (such as a remote server of the CareLink Network available from Medtronic, Inc. of Minneapolis, Minn.) or display an appropriate message that alerts the user (e.g., patient 12 or a clinician). Upon receiving the message via programmer 24, a clinician may perform imaging procedures, such as fluoroscopy, x-ray imaging, magnetic resonance imaging (MRI), or ultrasound imaging, to determine the location of lead 28, to determine the position of lead 28 within patient 12. Additionally or alternatively, IMD 16 may generate an alert that may be detected by patient 12. The alert may be an audible alert, such as a beeping sound, or a tactile alert, such as a vibration emitted by IMD 16 or programmer 24.

In some examples, programmer 24 may be a handheld computing device or a computer workstation. Programmer 24 may include a user interface that receives inputs from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some examples, a display of programmer 24 may include a touch screen display, and a user may interact with programmer 24 via the display.

A user, such as a physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of IMD 16.

For example, the user may use programmer 24 to retrieve information from IMD 16 regarding the rhythm of heart 14, trends therein over time or tachyarrhythmia episodes. As another example, the user may use programmer 24 to retrieve information from IMD 16 regarding other sensed physiological parameters of patient 12, such as electrical depolarization/repolarization signals from the heart (e.g., EGM signals), intracardiac or intravascular pressure, activity, posture, respiration or thoracic impedance.

The user may use programmer 24 to program a therapy progression for IMD 16. As one example, programmer 24 may select electrodes (i.e., an electrode combination) with which the cardiac therapy module of IMD 16 may deliver defibrillation pulses, select waveforms for the defibrillation pulse or select or configure a fibrillation detection algorithm for IMD 16. The user may also use programmer 24 to program aspects of other therapies provided by the cardiac therapy module of IMD 16, such as cardioversion or pacing therapies.

The user may also use programmer 24 to program aspects of the neurostimulation module. The therapy parameters for the neurostimulation module of IMD 16 may include an electrode combination for delivering neurostimulation signals, as well as an amplitude, which may be a current or voltage amplitude, and, if the neurostimulation module delivers electrical pulses, a pulse width, and a pulse rate for stimulation signals to be delivered to patient 12. The electrode combination may include a selected subset of one or more electrodes located on implantable lead 18 coupled to IMD 16 and/or a housing of IMD 16. The electrode combination may also refer to the polarities of the electrodes in the selected subset. By selecting particular electrode combinations, a clinician may target particular anatomic structures within patient 12. In addition, by selecting values for amplitude, pulse width, and pulse rate, the physician can attempt to generate an efficacious therapy for patient 12 that is delivered via the selected electrode subset.

As another example, the user may use programmer 24 to retrieve information from IMD 16 regarding the performance or integrity of IMD 16 or other components of the relevant therapy system 10, such as leads 18, 20, 22, 28 or a power source of IMD 16. With the aid of programmer 24 or another computing device, a user may select values for therapy parameters for controlling therapy delivery by the cardiac and neurostimulation modules of IMD 16. The values for the therapy parameters may be organized into a group of parameter values referred to as a "therapy program" or "therapy parameter set." "Therapy program" and "therapy parameter set" are used interchangeably herein.

Programmer 24 may communicate with IMD 16 via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
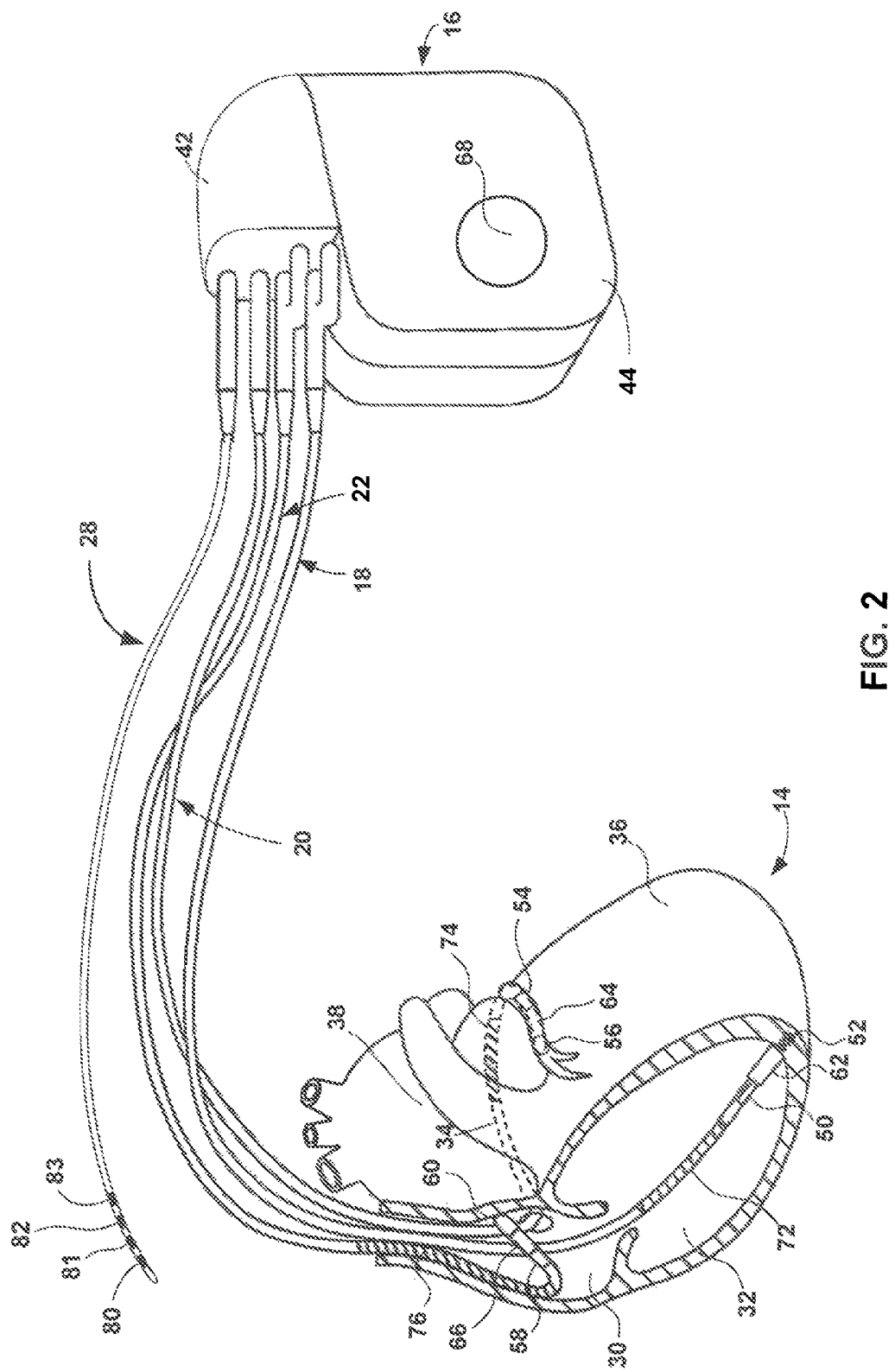
FIG. 2 is a conceptual diagram illustrating the IMD of FIG. 1 and the respective leads in greater detail.

FIG. 2 is a conceptual diagram illustrating IMD 16 and leads 18, 20, 22, and 28 of therapy system 10 in greater detail. In general, leads 18, 20, and 22 may be electrically coupled to the cardiac therapy module of IMD 16 and lead 28 may be electrically coupled to the neurostimulation module of IMD 16. In some examples, proximal ends of leads 18, 20, 22, and 28 may include electrical contacts that electrically couple to respective electrical contacts within connector block 42 of IMD 16. In addition, in some examples, leads 18, 20, 22, and 28 may be mechanically coupled to connector block 42 with the aid of set screws, connection pins or another suitable mechanical coupling mechanism.

Each of the leads 18, 20, 22, and 28 includes an elongated insulative lead body, which may carry a number of concentric coiled conductors separated from one another by tubular insulative sheaths. Other lead configurations are also contemplated, such as configurations that do not include coiled conductors. In the illustrated example, lead 18 includes electrodes 50, 52, and 72, lead 20 includes electrodes 54, 56, and 74, lead 22 includes electrodes 58, 60, and 76, and lead 28 includes electrodes 80-83. Bipolar electrodes 50 and 52 are located proximate to a distal end of lead 18. In addition, bipolar electrodes 54 and 56 are located proximate to a distal end of lead 20 and bipolar electrodes 58 and 60 are located proximate to a distal end of lead 22.

Electrodes 50, 54, and 58 may take the form of ring electrodes, and electrodes 52, 56, and 60 may take the form of extendable helix tip electrodes mounted retractably within insulative electrode heads 62, 64, and 66, respectively. Each of the electrodes 50, 52, 54, 56, 58, 60, 72, 74, and 76 may be electrically coupled to a respective one of the conductors within the lead body of its associated lead 18, 20, 22, and thereby coupled to respective ones of the electrical contacts on the proximal end of leads 18, 20 and 22.

Electrodes 50, 52, 54, 56, 58, 60, 72, 74, and 76 may sense electrical signals attendant to the depolarization and repolarization of heart 14. The electrical signals are conducted to IMD 16 via the respective leads 18, 20, 22. In some examples, IMD 16 also delivers pacing pulses via electrodes 50, 52, 54, 56, 58, and 60 to cause depolarization of cardiac tissue of heart 14. In some examples, IMD 16 includes one or more housing electrodes. In FIG. 2, IMD 16 includes a single housing electrode 68, which may be formed integrally with an outer surface of hermetically-sealed housing 44 of IMD 16 or otherwise coupled to housing 44. In some examples, housing electrode 68 is defined by an uninsulated portion of an outward facing portion of housing 44 of IMD 16. Other division between insulated and uninsulated portions of housing 44 may be employed to define two or more housing electrodes. In some examples, housing electrode 68 comprises substantially all of housing 44. Any of the electrodes 50, 52, 54, 56, 58, 60, 72, 74, and 76 may be used for unipolar sensing or pacing in combination with housing electrode 68. As described in further detail with reference to FIG. 4, housing 44 of IMD 16 may enclose a signal generator that generates cardiac pacing pulses and defibrillation or cardioversion shocks, as well as a sensing module for monitoring electrical cardiac signals of heart 14.

Leads 18, 20, and 22 also include elongated electrodes 72, 74, 76, respectively, which may take the form of a coil. IMD 16 may deliver defibrillation pulses to heart 14 via any combination of elongated electrodes 72, 74, 76, and housing electrode 68. Electrodes 68, 72, 74, 76 may also be used to deliver cardioversion pulses to heart 14. Electrodes 72, 74, 76 may be fabricated from any suitable electrically conductive material, such as, but not limited to, platinum, platinum alloy or other materials known to be usable in implantable defibrillation electrodes.

In particular, a sensing module of IMD 16 may sense electrical physiological signals of patient 12 via two or more of electrodes 50, 52, 54, 56, 58, 60, 72, 74, and 76. The electrical signals may be used by the cardiac therapy module of IMD 16 to modulate therapy. The cardiac therapy module of IMD 16 may deliver pacing pulses via any combination of electrodes 50, 52, 54, 56, 58, 60, 72, 74, and 76 and housing electrode 68, e.g., any unipolar or bipolar electrode configuration, or cause depolarization of cardiac tissue of heart 14. The cardiac therapy module of IMD 16 may alternatively or additionally deliver defibrillation and/or cardioversion pulses to heart 14 via electrodes 50, 52, 54, 56, 58, 60, 72, 74, and 76. Electrodes 72, 74, and 76 may be useful in delivering high energy defibrillation pulses to heart 14.

Leads 18, 20, and 22 and lead 28 may be utilized to deliver different therapies. For example, the cardiac module of IMD 16 may deliver therapy directly to heart 14, e.g., pacing, cardioversion, and/or defibrillation signals and neurostimulation module may deliver stimulation signals to a tissue site proximate a nerve. In some examples, neurostimulation lead 28 is implanted intravascularly within jugular vein 46 (FIG. 1) and proximate to the vagus nerve of patient 12. With respect to FIG. 1, lead 28 is implanted at target tissue site 40 which is proximate to a vagus nerve and located a sufficient distance away from heart 14 such that neurostimulation therapy is not likely to capture heart 14. In some examples, a clinician may implant leads 18, 20, 22, and 28 in any order because each of the leads may be inserted into the jugular vein 46 through the same opening.

When implanted, the neurostimulation module of IMD 16 may deliver neurostimulation via any combination of electrodes 80, 81, 82, 83 carried by lead 28 and housing electrode 68. In general, the neurostimulation module of IMD 16 delivers neurostimulation to the vagus nerve (not shown) of patient 12. In some examples, the neurostimulation module may deliver a stimulation signal between one of electrodes 80-83 and housing electrode 68, i.e., in a unipolar configuration. As another example, the neurostimulation module may deliver a stimulation signal between a plurality of electrodes 80-83, e.g., in a bipolar configuration.

In some examples, electrodes 80-83 may take the form of ring, partial ring or segmented electrodes. Ring electrodes may be relatively simple to program, in comparison to a complex electrode array geometry described below, and are capable of delivering an electrical field to any tissue adjacent to the respective electrodes 80-83, such as tissue at target tissue site 40, including tissue proximate to the vagus nerve and laryngeal muscle tissue. In other examples, at least one of the electrodes 80-83 may have a different configuration. For example at least one of electrodes 80-83 may take the form an extendable helix tip electrode. The helix tip electrode may be mounted retractably within an insulative electrode heads similar to that of insulative electrode heads 62, 64, and 66 of leads 18, 20, 22. The extendable tip electrode may be useful for fixing lead 28 within jugular vein 46 (FIG. 1). For example, the helix may be introduced into the wall of jugular vein 46 proximate to target tissue site 40 for the neurostimulation therapy.

In other examples, at least one of the electrodes 80-83 may have a complex electrode array geometry that is capable of producing shaped electrical fields. The complex electrode array geometry may include multiple electrodes (e.g., partial ring or segmented electrodes) around the outer perimeter of lead 28, rather than one ring electrode. In the example shown in FIG. 2, lead 28 includes four electrodes 80-83, but may include any suitable number of electrodes, such as fewer than four electrodes or greater than four electrodes (e.g., eight or sixteen electrodes). One or more of electrodes 28 may also be used for sensing electrical activity of patient 12, such as electrical cardiac signals, EMG signals of tissue proximate to target tissue site 40, or electrical nerve signals. Lead 28 may also include one or more sensors that generate an electrical signal based on a physiological parameter, such as a pressure sensor that converts vibrations of laryngeal muscle into an electrical signal.

The configuration, type, and number of electrodes 80-83 and lead 28 illustrated in FIG. 2 is merely exemplary. In other examples, IMD 16 may be coupled to any suitable number of neurostimulation leads with any suitable number and configuration of electrodes for delivering neurostimulation therapy to a target tissue site. Moreover, lead 28 may comprise a shape other than a cylindrical shape. As an example, lead 28 may comprise a paddle-shaped portion that carries electrodes 80-83.

In other examples of therapy systems that provide cardiac and neurostimulation therapy to patient 12, a therapy system may include any suitable number of leads coupled to IMD 16. For example, other examples of therapy systems may include fewer than or more than three transvenous leads, such as a single lead that is coupled to the cardiac therapy module of IMD 16 and extends into right atrium 30 or right ventricle 32, or two leads that extend into a respective one of the right ventricle 32 and right atrium 30 (shown in FIG. 3). In other examples a suitable number of leads coupled to a cardiac therapy module of IMD 16 may be implanted proximate to, but outside of heart 14 (referred to as extravascular leads). Electrodes carried by extravascular leads may comprise subcutaneous, submuscular, epicardial, and/or intramural electrodes.

Figure 3:
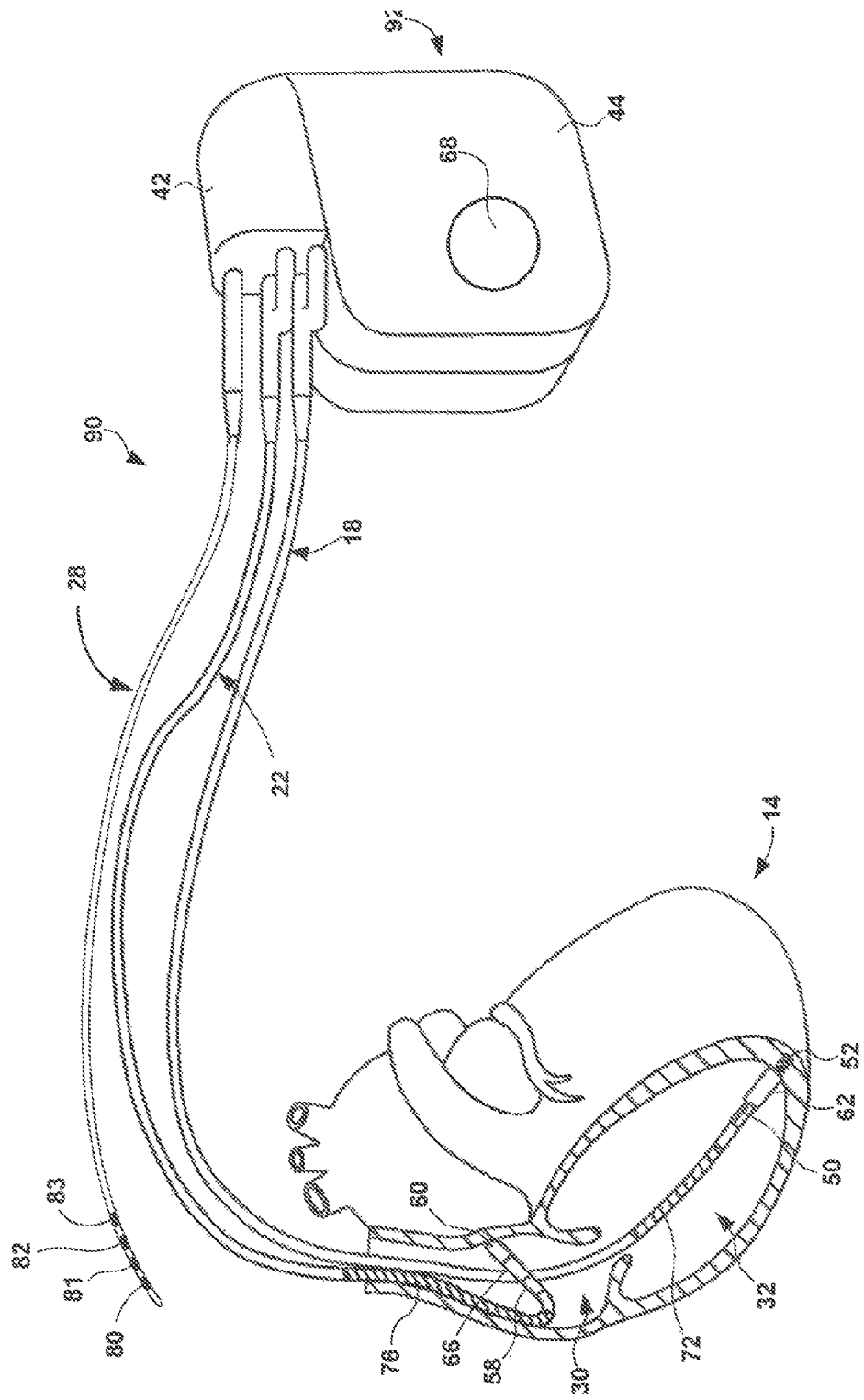
FIG. 3 is a conceptual diagram illustrating another exemplary IMD lead configuration.

FIG. 3 is a conceptual diagram illustrating an example therapy system 90, which includes IMD 92 electrically connected to two cardiac leads 18, 22, rather than three leads as shown in FIGS. 1 and 2, and neurostimulation lead 28. Leads 18, 22 are implanted within right ventricle 32 and right atrium 30, respectively. Therapy system 90 shown in FIG. 2 may be useful for providing defibrillation and pacing pulses to heart 14. IMD 92 operates similar to IMD 16 (FIGS. 1 and 2) and includes a cardiac therapy module for delivering defibrillation and pacing pulses to heart 14 and a neurostimulation module for delivering neurostimulation at target tissue site 40 to modulate an autonomic nervous system of patient 12. In particular, IMD 92 may also include various features attributed to IMD 16 herein, such as the features used to determine whether electrodes 80-83 of leads 28 have migrated away from target tissue site 40 (FIG. 1) and towards heart 14.

FIG. 4 is a functional block diagram of an example configuration of IMD 16, which includes processor 100, memory 102, cardiac therapy module 104, neurostimulation therapy module 106, telemetry module 108, power source 110, and lead migration detection module 120. Cardiac therapy module 104 includes signal generator 112 and sensing module 114. Neurostimulation therapy module 106 includes signal generator 116 and sensing module 118. The components of IMD 16 shown in FIG. 4 may be substantially enclosed within a common, hermetically sealed outer housing 44 of IMD 16. Although cardiac therapy module 104 and neurostimulation therapy module 106 are illustrated as separate modules in FIG. 4, in some examples, cardiac therapy module 104 and neurostimulation module 106 and their respective components may share circuitry. For example, signal generators 112 and 116 may share common circuitry, e.g., a stimulation engine, charging circuitry, capacitors, and the like. As an example, in examples in which cardiac therapy module 104 and neurostimulation module 106 deliver stimulation in alternation, cardiac therapy module 104 and neurostimulation module 106 may share some or all stimulation generation circuitry. Similarly, in some examples, sensing modules 114 and 118 may also share common circuitry, such as an analog-to-digital converters and the like.

Memory 102 includes computer-readable instructions that, when executed by processor 100, cause IMD 16 and processor 100 to perform various functions attributed to IMD 16 and processor 100 herein. In FIG. 4, memory 102 includes cardiac rhythm management therapy programs 122 that define the parameters with which cardiac therapy module 104 generates cardiac rhythm management therapy for delivery to heart 14, and neurostimulation programs 124 that define the parameters with which neurostimulation module 106 generates neurostimulation therapy for delivery to target tissue site 40. Memory 102 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 100 may include any one or more of a microprocessor, a controller, a digital signal processor (DSP), an application specific integrated circuit (ASIC), a field-programmable gate array (FPGA), or equivalent discrete or integrated logic circuitry. In some examples, processor 100 may include multiple components, such as any combination of one or more microprocessors, one or more controllers, one or more DSPs, one or more ASICs, or one or more FPGAs, as well as other discrete or integrated logic circuitry. The functions attributed to processor 100 herein may be embodied as software, firmware, hardware or any combination thereof. Processor 100 may control cardiac therapy module 104 to deliver stimulation therapy according to a selected one or more of cardiac rhythm management programs 122 stored in memory 102. In addition, processor 100 may control neurostimulation module 106 to delivering stimulation therapy according to a selected one or more of neurostimulation programs 124 stored in memory 102. Specifically, processor 100 may control cardiac therapy module 104 and/or neurostimulation module 106 to deliver electrical signals with the amplitudes, frequency, electrode polarities, and, in the case of stimulation pulses, pulse widths specified by the selected one or more cardiac and neurostimulation therapy programs 122, 124, respectively.

In the example shown in FIG. 4, cardiac therapy module 104 is electrically connected to electrodes 50, 52, 54, 56, 58, 60, 72, 74, and 76 of leads 18, 20, and 22 and housing electrode 68, and neurostimulation module 106 is electrically connected to electrodes 80-83 of lead 28 and housing electrode 68. In other examples, cardiac therapy module 104 and neurostimulation module 106 may be coupled to any suitable number of electrodes, which may comprise a greater number of electrodes or a fewer number of electrodes.

Cardiac therapy module 104 is configured to generate and deliver cardiac rhythm therapy to heart 14. For example, signal generator 112 of cardiac therapy module 104 may generate and deliver cardioversion or defibrillation shocks and/or pacing pulses to heart 14 via a select combination of electrodes 50, 52, 54, 56, 58, 60, 72, 74, and 76 and housing electrode 68. Stimulation generator 112 of cardiac therapy module 104 is electrically coupled to electrodes 50, 52, 54, 56, 58, 60, 72, 74, and 76, e.g., via conductors of the respective lead 18, 20, 22, or, in the case of housing electrode 68, via an electrical conductor disposed within housing 44 of IMD 16. Stimulation generator 112 is configured to generate and deliver cardiac rhythm management therapy to heart 14. For example, stimulation generator 112 may deliver defibrillation shocks to heart 14 via at least two electrodes 68, 72, 74, 76. Signal generator 112 may deliver pacing pulses via ring electrodes 50, 54, 58 coupled to leads 18, 20, and 22, respectively, and/or helical electrodes 52, 56, and 60 of leads 18, 20, and 22, respectively. In some examples, signal generator 112 delivers pacing, cardioversion, or defibrillation therapy in the form of electrical pulses. In other examples, signal generator 112 may deliver one or more of these types of stimulation in the form of other signals, such as sine waves, square waves, or other substantially continuous time signals.

Although not shown in FIG. 4, in some examples, cardiac therapy module 104 may include a switching module to selectively couple electrodes 50, 52, 54, 56, 58, 60, 72, 74, and 76 to signal generator 112 and/or sensing module 114. The switching module may include a switch array, switch matrix, multiplexer, or any other type of switching device suitable to selectively couple stimulation energy to selected electrodes. In other examples, however, stimulation generator 112 may independently deliver stimulation to electrodes 50, 52, 54, 56, 58, 60, 72, 74, and 76 or selectively sense via one or more of electrodes 50, 52, 54, 56, 58, 60, 72, 74, and 76 without a switch matrix.

Sensing module 114 monitors signals from at least one of electrodes 50, 52, 54, 56, 58, 60, 72, 74, and 76 in order to monitor electrical activity of heart 14, e.g., via an EGM or ECG signal. In some examples, sensing module 114 includes a switching module (not shown in FIG. 4) to select a particular subset of available electrodes to sense the heart activity. Processor 100 may, in some examples, select the electrodes that function as sense electrodes via the switching module within sensing module 114, e.g., by providing signals via a data/address bus. In some examples, sensing module 114 includes one or more sensing channels, each of which may comprise an amplifier. In response to the signals from processor 100, the switching module of within sensing module 114 may couple the outputs from the selected electrodes to one of the sensing channels.

One channel of sensing module 114 may include an R-wave amplifier that receives signals from electrodes 50 and 52, which are used for pacing and sensing in right ventricle 32 of heart 14. Another channel may include another R-wave amplifier that receives signals from electrodes 54 and 56, which are used for pacing and sensing proximate to left ventricle 36 of heart 14. In some examples, in one operating mode of sensing module 114, the R-wave amplifiers may take the form of an automatic gain controlled amplifier that provides an adjustable sensing threshold as a function of the determined R-wave amplitude of the heart rhythm.

In addition, in some examples, one channel of sensing module 114 may include a P-wave amplifier that receives signals from electrodes 58 and 60, which are used for pacing and sensing in right atrium 30 of heart 14. In some examples, in one operating mode of sensing module 114, the P-wave amplifier may take the form of an automatic gain controlled amplifier that provides an adjustable sensing threshold as a function of the determined P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS." Other suitable amplifiers may also be used. Furthermore, in some examples, one or more of the sensing channels of sensing module 114 may be selectively coupled to housing electrode 68, or elongated electrodes 72, 74, or 76, with or instead of one or more of electrodes 50, 52, 54, 56, 58 or 60, e.g., for unipolar sensing of R-waves or P-waves in any of chambers 30, 32, or 36 of heart 14.

In some examples, sensing module 114 includes a channel that comprises an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 102 as an EGM. In some examples, the storage of such EGMs in memory 102 may be under the control of a direct memory access circuit. Processor 100 may employ digital signal analysis techniques to characterize the digitized signals stored in memory 102 to detect and classify the patient's heart rhythm from the electrical signals. Processor 100 may detect and classify the heart rhythm of patient 12 by employing any of the numerous signal processing methodologies known in the art.

If cardiac therapy module 104 is configured to generate and deliver pacing pulses to heart 14, processor 100 may include pacer timing and control module, which may be embodied as hardware, firmware, software, or any combination thereof. The pacer timing and control module may comprise a dedicated hardware circuit, such as an ASIC, separate from other processor 100 components, such as a microprocessor, or a software module executed by a component of processor 100, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within processor 100 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals from sensing module 114 to blank one or more channels, e.g., amplifiers, for a period during and after delivery of electrical stimulation to heart 14. The durations of these intervals may be determined by processor 100 in response to stored data in memory 102. The pacer timing and control module of processor 100 may also determine the amplitude of the cardiac pacing pulses.

During pacing, escape interval counters within the pacer timing/control module of processor 100 may be reset upon sensing of R-waves and P-waves. Signal generator 112 may include pacer output circuits that are coupled, e.g., selectively by a switching module, to any combination of electrodes 50, 52, 54, 56, 58, 60, 68, 72, 74, and 76 appropriate for delivery of a bipolar or unipolar pacing pulse to one of the chambers of heart 14. Processor 100 may reset the escape interval counters upon the generation of pacing pulses by signal generator 112, and thereby control the basic timing of cardiac pacing functions, including anti-tachyarrhythmia pacing.

The value of the count present in the escape interval counters when reset by sensed R-waves and P-waves may be used by processor 100 to determine the durations of R-R intervals, P-P intervals, P-R intervals and R-P intervals, which are measurements that may be stored in memory 102. Processor 100 may use the count in the interval counters to detect a tachyarrhythmia event, such as ventricular fibrillation event or ventricular tachycardia event. Upon detecting a threshold number of tachyarrhythmia events, processor 100 may identify the presence of a tachyarrhythmia episode, such as a ventricular fibrillation episode, a ventricular tachycardia episode, or a non-sustained tachycardia (NST) episode. Examples of tachyarrhythmia episodes that may qualify for delivery of responsive therapy include a ventricular fibrillation episode or a ventricular tachyarrhythmia episode. In the case of a NST, however, the count in the interval counters may not meet the requirements for triggering a therapeutic response.

In some examples, processor 100 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 100 and any updating of the values or intervals controlled by the pacer timing and control module of processor 100 may take place following such interrupts. A portion of memory 102 may be configured as a plurality of recirculating buffers, capable of holding series of measured intervals, which may be analyzed by processor 100 in response to the occurrence of a pace or sense interrupt to determine whether heart 14 of patient 12 is presently exhibiting atrial or ventricular tachyarrhythmia.

In some examples, an arrhythmia detection method may include any suitable tachyarrhythmia detection algorithms. In one example, processor 100 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. However, other arrhythmia detection methodologies may also be employed by processor 100 in other examples.

In the examples described herein, processor 100 may identify the presence of an atrial or ventricular tachyarrhythmia episode by detecting a series of tachyarrhythmia events (e.g., R-R or P-P intervals having a duration less than or equal to a threshold) of an average rate indicative of tachyarrhythmia or an unbroken series of short R-R or P-P intervals. The thresholds for determining the R-R or P-P interval that indicates a tachyarrhythmia event may be stored within memory 102 of IMD 16. In addition, the number of tachyarrhythmia events that are detected to confirm the presence of a tachyarrhythmia episode may be stored as a number of intervals to detect (NID) threshold value in memory 102. In some examples, processor 100 may also identify the presence of the tachyarrhythmia episode by detecting a variability of the intervals between tachycardia events. For example, if the interval between successive tachyarrhythmia events varies by a particular percentage or the differences between the coupling intervals are higher than a given threshold over a predetermined number of successive cycles, processor 100 may determine that the tachyarrhythmia is present.

If processor 100 detects an atrial or ventricular tachyarrhythmia based on signals from sensing module 114, and an anti-tachyarrhythmia pacing regimen is desired, timing intervals for controlling the generation of anti-tachyarrhythmia pacing therapies by signal generator 112 may be loaded by processor 100 into the pacer timing and control module to control the operation of the escape interval counters therein and to define refractory periods during which detection of R-waves and P-waves is ineffective to restart the escape interval counters.

If cardiac therapy module 104 is configured to generate and deliver defibrillation pulses to heart 14, signal generator 112 may include a high voltage charge circuit and a high voltage output circuit. In the event that generation of a cardioversion or defibrillation pulse is required, processor 100 may employ the escape interval counter to control timing of such cardioversion and defibrillation pulses, as well as associated refractory periods. In response to the detection of atrial or ventricular fibrillation or tachyarrhythmia requiring a cardioversion pulse, processor 100 may activate a cardioversion/defibrillation control module, which may, like pacer timing and control module, be a hardware component of processor 100 and/or a firmware or software module executed by one or more hardware components of processor 100. The cardioversion/defibrillation control module may initiate charging of the high voltage capacitors of the high voltage charge circuit of signal generator 112 under control of a high voltage charging control line.

Processor 100 may monitor the voltage on the high voltage capacitor, e.g., via a voltage charging and potential (VCAP) line. In response to the voltage on the high voltage capacitor reaching a predetermined value set by processor 100, processor 100 may generate a logic signal that terminates charging. Thereafter, timing of the delivery of the defibrillation or cardioversion pulse by signal generator 112 is controlled by the cardioversion/defibrillation control module of processor 100. Following delivery of the fibrillation or tachycardia therapy, processor 100 may return signal generator 112 to a cardiac pacing function and await the next successive interrupt due to pacing or the occurrence of a sensed atrial or ventricular depolarization.

Signal generator 112 may deliver cardioversion or defibrillation pulses with the aid of an output circuit that determines whether a monophasic or biphasic pulse is delivered, whether housing electrode 68 serves as cathode or anode, and which electrodes are involved in delivery of the cardioversion or defibrillation pulses. Such functionality may be provided by one or more switches or a switching module of signal generator 112.

Neurostimulation module 106 is configured to generate and deliver electrical stimulation therapy to a tissue site proximate a nerve or a nonmyocardial or extravascular cardiac tissue site, e.g., in order to modulate an autonomic nervous system or modulate vascular tone. Example stimulation sites for neurostimulation module 106 include, but are not limited to, tissue proximate a vagus nerve, braches of vagus nerve, or spinal cord of patient 12. For example, signal generator 116 may generate stimulation signals that are delivered to a tissue site proximate a vagus nerve via a select combination of electrodes 80-83 of lead 28 and/or housing electrode 68. The stimulation signals may be pulses as primarily described herein, or continuous time signals, such as sine waves.

Signal generator 116 may be a single or multi-channel signal generator. In particular, signal generator 116 may be capable of delivering, a single stimulation pulse, multiple stimulation pulses, or a continuous signal at a given time via a single electrode combination or multiple stimulation pulses at a given time via multiple electrode combinations. In some examples, however, neurostimulation therapy module 106 may be configured to deliver multiple channels on a time-interleaved basis. In this case, neurostimulation therapy module 106 may include a switching module (not shown) that serves to time division multiplex the output of the signal generator across different electrode combinations at different times to deliver multiple programs or channels of stimulation energy to patient 12.

Although not shown in FIG. 4, in some examples, neurostimulation therapy module 106 may include a switching module to selectively couple electrodes 68, 80-83 to signal generator 116 and/or sensing module 118. The switching module may couple stimulation signals to selected conductors within lead 28, which, in turn, deliver the stimulation signals across selected electrodes. The switching module may be a switch array, switch matrix, multiplexer, or any other type of switching device suitable to selectively couple stimulation energy to selected electrodes.

Processor 100 may control cardiac therapy module 104 and neurostimulation therapy module 106 to coordinate the delivery of electrical stimulation to patient 12. As previously described, in some examples, neurostimulation therapy module 106 may deliver neurostimulation signals to patient 12 at substantially the same time as pacing, cardioversion, and/or defibrillation pulses delivered by cardiac therapy module 104. In those examples, processor 100 may control cardiac therapy module 104 and neurostimulation module 106 to generate and deliver electrical stimulation at substantially the same time.

In other examples, in addition to or instead of delivering neurostimulation signals at substantially the same time that cardiac therapy module 104 delivers stimulation, neurostimulation module 106 may deliver neurostimulation signals to patient 12 prior to or after cardiac therapy module 104 delivers stimulation. Thus, in some examples, processor 100 may control cardiac therapy module 104 and neurostimulation therapy module 106 to deliver therapy to patient 12 at different times. In some examples, processor 100 may control neurostimulation module 106 to deliver neurostimulation signals to patient 12 based on physiological parameter values sensed by sensing module 114 of cardiac therapy module 104 of sensing module 118 of neurostimulation therapy module 160, which may indicate the presence of an arrhythmia.

In other examples, processor 100 may control neurostimulation therapy module 106 to deliver neurostimulation signals to patient 12 according to a predetermined schedule that is independent of physiological parameter values sensed by sensing module 114. The schedule may be determined by a clinician and stored in memory 102. As previously indicated, the delivery of electrical stimulation by neurostimulation module 106 to modulate an autonomic system of the patient's nervous system may help regulate the patient's heart rate. Thus, processor 100 may control neurostimulation module 106 to generate and deliver neurostimulation signals to patient 12 as a preventative measure, e.g., to reduce the occurrence of arrhythmias, and, therefore, reduce the frequency with which cardiac therapy module 104 generate and delivers stimulation.

Telemetry module 108 includes any suitable hardware, firmware, software or any combination thereof for communicating with another device, such as programmer 24 (FIG. 1). Under the control of processor 100, telemetry module 108 may receive downlink telemetry from and send uplink telemetry to programmer 24 with the aid of an antenna, which may be internal and/or external. Processor 100 may provide the data to be uplinked to programmer 24 and the control signals for the telemetry circuit within telemetry module 108, e.g., via an address/data bus. In some examples, telemetry module 108 may provide received data to processor 100 via a multiplexer.

In some examples, processor 100 may transmit atrial and ventricular heart signals (e.g., also referred to as cardiac signals, and can include, for example, EGM signals) produced by sensing module 114 to programmer 24. In some examples, programmer 24 interrogates IMD 16 to retrieve the heart signals, while in other examples, IMD 16 automatically transmits the heart signals to programmer 24. Processor 100 may store heart signals within memory 102, and retrieve stored heart signals from memory 102. Processor 100 may also generate and store marker codes indicative of different cardiac episodes that sensing module 114 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983.

Processor 100 may also control telemetry module 108 to transmit an alert signal to programmer 24 when processor 100 determines that lead 28 has migrated from target tissue site 40. That is, when IMD 16 determines that lead 28 has migrated from target tissue site 40, processor 100 may withhold delivery of stimulation by neurostimulation module 106 and cause telemetry module 108 to transmit an alert signal to programmer 24. Programmer 24 may display a message via a monitor that alerts the user that lead 28 has migrated from target tissue site 40 and that neurostimulation is suspended. Programmer 24 may also generate an audible or tactile alert in response to receiving the alert message/signal from IMD 16.

The various components of IMD 16 are coupled to power source 100, which may include a rechargeable or non-rechargeable battery or a supercapacitor. A non-rechargeable battery may be selected to last for several years, while a rechargeable battery may be inductively charged from an external device, e.g., on a daily or weekly basis.

In some examples, data generated by sensing module 114 or sensing module 118 and stored in memory 102 may be uploaded to a remote server, from which a clinician or another user may access the data to determine whether a potential lead migration issue exists. An example of a remote server includes the CareLink Network, available from Medtronic, Inc. of Minneapolis, Minn. An example system may include an external device, such as a server, and one or more computing devices that are coupled to IMD 16 and programmer 24 via a network.

In accordance with various examples described in this disclosure, processor 100 of IMD 16 may implement one or more of the previously described techniques in order to determine whether neurostimulation should be withheld from patient 12 or otherwise modified because electrodes 80-83 of lead 28 have migrated from target tissue site 40 and toward heart 14. IMD 16 may periodically or substantially continuously monitor the relative location of electrodes 80-83 of lead 28 and target tissue site 40 (or heart 14). For example, IMD 16 may perform one or more of the lead migration detection techniques according to a schedule stored in memory 102. The schedule may cause IMD 16 to execute the migration detection technique on a daily basis, an hourly basis, or several times per day, such as approximately every twenty minutes, fifteen minutes, ten minutes, five minutes, or approximately every minute. Alternatively, IMD 16 may continuously repeat one or more of the migration detection techniques. Other frequencies with which IMD 16 may determine whether electrodes 80-83 of lead 28 have moved are also contemplated.

In the example shown in FIG. 4, processor 100 includes lead migration detection module 120, which may be implemented with a dedicated processor, logic circuitry, or may be part of processor 100, such as dedicated firmware. In operation, lead migration detection module 120 controls operation of and process information received from one or more of cardiac therapy module 104 and neurostimulation therapy module 106. As one example, lead migration detection module 120 may control operation of neurostimulation therapy module 106 to determine whether lead 28 has migrated to the extent that there is loss of nerve capture by electrodes 80-83. In accordance with the techniques implemented by lead migration detection module 120, which are described below, lead migration detection module 120 may include filters, comparators, correlators (matched filters), analog-to-digital converters (ADCs), sample-and-hold circuitry, or other signal processing and/or logic circuitry for analyzing sensed electrical signals, near field cardiac signals (e.g., ECG or EGM signals), and far field cardiac signals (ECG or EGM signals).

Lead migration detection module 120 may control signal generator 116 to generate and deliver a test electrical stimulation signal to patient 12 via one or more of electrodes 80-83 of lead 28. For example, lead migration detection module 120 may control signal generator 116 to deliver the test signal prior to delivering neurostimulation to patient 12 in order to determine whether electrodes 80-83 are at least a predetermined distance away from heart 14. The predetermined distance can be, for example, a minimum distance at which electrical stimulation delivered via electrodes 80-83 does not capture heart 14. In this way, the predetermined distance can indicate a relative location of electrodes 80-83 relative to heart 14. As discussed above, a physiological response to the test signal may indicate whether electrodes 80-83 are at least the predetermined distance away from heart 14. In some examples, lead migration detection module 120 may generate a test electrical stimulation signal with electrodes 80, 81, which are located closer to a distal tip of lead 28 than electrodes 82, 83, and, in some cases, may provide a better indication of whether electrodes 80-83 have migrated toward heart 14 because electrodes 80, 81 may be closer to heart 14 than electrodes 82, 83 when lead 28 migrates.

Lead migration detection module 120 may also control signal generator 116 to deliver a test signal via the electrodes located at the most distal end of lead 28, i.e., electrodes 80 and 81 (FIGS. 2 and 3). The test electrical stimulation signal may be a single pulse or other pulse waveform or continuous signal. In some examples, lead migration detection module 120 controls signal generator 116 to deliver the test signal during the ventricular refractory period. In other words, the test signal may be coupled to an R-wave. For example, the test stimulation signal waveform may have a relatively low frequency, such as a frequency of about 1 Hz. The test stimulation signal may or may not provide therapeutic benefits to patient 12. The stimulation parameter values for the test stimulation signal may be stored as a neurostimulation program 124 in memory 102. Lead migration detection module 120 may then control sensing module 118 to sense an electrical signal indicative of a physiological response to the stimulation signal, and analyze the sensed electrical signal provided by sensing module 118. If lead migration detection module 120 determines the physiological response (e.g., as indicated by the sensed electrical signal) indicates there is loss of nerve capture, lead migration detection module 120 may control neurostimulation therapy module 106 and, more particularly, stimulation module 116, to suspend the delivery of neurostimulation to patient 12 or otherwise adjust the delivery of neurostimulation therapy to patient 12 (e.g., adjust a stimulation parameter, such as a frequency, amplitude, pulse width, and the like to decrease the possibility that a neurostimulation signal will capture heart 14).

In some examples, sensing module 118 may sense an electrical nerve signal between two or more of electrodes 80-83 and output the electrical nerve signal to lead migration detection module 120. The electrical nerve signal may be an electrical signal generated by a vagus nerve in response to the delivery of the test electrical stimulation signal by signal generator 116. The electrical nerve signal may indicate whether lead 28 has migrated away from target tissue site 40, which may, in turn, indicate whether lead 28 has migrated towards heart 14. An example electrical nerve signal is shown and described with respect to FIG. 7. In some examples, the electrical nerve signal may be an electroneurogram (ENG) that is generated by sensing module 118. An ENG may indicate the electrical activity of neurons of the vagus nerve (or other target nerve for the neurostimulation therapy).

If the test electrical stimulation delivered by signal generator 116 captures the vagus nerve, the electrical nerve signal generated by the vagus nerve may indicate the physiological response to the test stimulation signal. In some examples, lead migration detection module 120 may determine whether the vagus nerve was captured by the test stimulation signal by measuring an amplitude of the electrical nerve signal and comparing the determined amplitude value to a predetermined threshold value stored in memory 102. A determined amplitude value of the sensed electrical nerve signal that is less than the threshold value may indicate a loss of nerve capture by electrodes 80-83 of lead 28. The loss of nerve capture may be a result of migration of electrodes 80-83 from target tissue site 40 (FIG. 1). As previously described, lead migration detection module 120 may control neurostimulation module 106 to withhold the delivery of neurostimulation to patient 12 or otherwise adjust the neurostimulation therapy parameters when a loss of nerve capture is detected. The loss of nerve capture may indicate that electrodes 80-83 have migrated toward heart 14.

In other examples, sensing module 118 may sense a physiological response to the test stimulation signal delivered by signal generator 116 of neurostimulation module 106 by sensing movement (e.g., vibrations or contraction) of muscle that is proximate target tissue site 40 (FIG. 1). The muscle may be stimulated by the test stimulation signal because of the proximity of the muscle to electrodes 80-83 on lead 28 or because the muscle is innervated by the target nerve (e.g., vagus nerve), which is stimulated by the test stimulation signal. In some examples, sensing module 118 may sense vibrations generated by laryngeal muscle tissue proximate to target tissue site 40. Sensing module 118 may be electrically connected to a sensor that that generates an electrical signal indicative of the muscle movement, such as a pressure sensor, an acoustic sensor, an accelerometer, piezoelectric sensor, and the like. The sensor indicative of muscle movement may be on lead 28 or another lead. Alternatively, the pressure sensor, acoustic sensor, accelerometer, or piezoelectric sensor may be located within housing 44 of IMD 16 and electrically coupled to sensing module 118, or may be a separately implanted sensor that communicates with IMD 16. In some examples, sensing module 118 may generate an EMG, which indicates the electrical potential generated by muscle cells when the cells contract.

Sensing module 118 may output the sensed electrical signal indicative of muscle movement to lead migration detection module 120. Lead migration detection module 120 may analyze the sensed electrical signal to determine whether a characteristic of the signal indicates the loss of nerve capture. If electrodes 80-83 are located proximate the target nerve, the delivery of the test stimulation signal may capture the target nerve, and the muscle innervated by the target nerve may move in response to the delivery of the test stimulation signal. Thus, if the characteristic of the sensed electrical muscle signal indicates a low level of muscle movement, the electrical muscle signal may indicate the loss of nerve capture. Loss of nerve capture (e.g., a decrease in nerve capture or a complete loss of nerve capture) by the stimulation delivered by neurostimulation therapy module 106 may indicate that neurostimulation lead 28 has migrated from target tissue site 40.

Lead migration detection module 120 may compare the characteristic of the sensed electrical muscle signal to a threshold value stored within memory 102 to determine whether the sensed electrical signal is indicative of an expected physiological response to the test stimulation signal when electrodes 80-83 are located within a sufficient distance to the target nerve, e.g., at target tissue site 40. If the characteristic of the sensed electrical muscle signal is less than or equal to the threshold value, lead migration detection module 120 may determine that electrodes 80-83 of lead 28 have moved and there is a loss of nerve capture. Thus, if the characteristic of the sensed electrical muscle signal is less than or equal to the threshold value, processor 100 may control neurostimulation therapy module 106 to suspend or otherwise adjust the delivery of stimulation to patient 12.

In some examples, the characteristic of the sensed electrical muscle signal may include a frequency or amplitude of the electrical signal. Lead migration detection module 120 may determine the frequency of sensed electrical muscle signal by applying an analog-to-digital converter (ADC) and performing a Fast Fourier Transform (FFT) on the digital signal. Alternatively, lead migration detection module 120 may use a peak amplitude detector to determine the number of amplitude peaks over a given time period and, thus, the frequency of the sensed electrical signal. In any case, the frequency of the signal may change as the distance between the laryngeal muscle tissue and lead 28 increases. Accordingly, in some examples, lead migration detection module 120 may control neurostimulation module 106 to withhold the delivery of neurostimulation to patient 12 or otherwise adjust neurostimulation therapy based on the comparison of the determined frequency to a threshold frequency stored in memory 102.

Cardiac capture is another physiological response that lead migration detection module 120 may monitor for following the delivery of the test stimulation signal by signal generator 116 in order to determine whether electrodes 80-83 have migrated away from target tissue site 40 and toward heart 14. Lead migration detection module 120 may control operation of neurostimulation module 106 to determine whether there is cardiac capture. When lead migration detection module 120 determines that there is cardiac capture, lead migration detection module 120 may control neurostimulation module 106 to withhold or otherwise adjust the delivery of delivering neurostimulation to patient 12 because the cardiac capture may indicate electrodes 80-83 have migrated toward heart 14.

As described above with respect to the technique for detecting loss of nerve capture, lead migration detection module 120 may cause signal generator 116 to deliver a test electrical stimulation signal to target tissue site 40 via a select combination of electrodes 80-83 of lead 28. In some examples, the test stimulation signal may comprise a frequency of about 1 Hz and an amplitude of about 8 volts (V). In some examples, the voltage or current amplitude of the test signal may be greater than the planned voltage or current amplitude value for therapy to provide a guard band.

Instead of or in addition to detecting a signal indicative of nerve capture, lead migration detection module 120 may detect an electrical cardiac signal indicative of cardiac activity of heart 14 in response to the delivery of the test electrical signal. The cardiac signal may comprise, for example, an ECG or EGM signal generated by sensing module 114 of cardiac therapy module 104 or sensing module 118 of neurostimulation therapy module 106. Sensing module 114 may generate a (near) field cardiac signal (e.g., a near field ECG or EGM signal) under the control of lead migration detection module 120 for a period of time following delivery of the test stimulation pulse by signal generator 116. In particular, sensing module 114 may sense the cardiac signal via select electrodes of leads 18, 20, and 22. Lead migration detection module 120 may analyze the sensed cardiac signal to detect a physiological response, e.g., an evoked response, to the test stimulation signal delivered by signal generator 116.

The response by heart 14 evoked by the delivery of the test stimulation signal (the "evoked response") may take various forms. For this reason, a clinician may determine one or more characteristics of a sensed cardiac signal that indicate the evoked response caused by lead 28 migrating from target tissue site 40 during a trial stage, such as during implantation of therapy system 10 in patient 12. As an example, the clinician may position lead 28 proximate heart 14 and deliver test stimulation signals via signal generator 116. The clinician may then sense a cardiac signal with a select combination of electrodes of leads 18, 20, 22, and 28 to determine one or more characteristics of the cardiac signal that indicate the test stimulation signals captured heart 14, e.g., paced heart 14. The characteristic of the sensed cardiac signal that indicates cardiac capture by the test stimulation signal may indicate, for example, depolarization artifacts that follow the delivery of the test stimulation signal. The depolarization artifacts present in the sensed cardiac signal may include, for example, an R-wave, a P-wave or other components of a QRS complex of a sinus rhythm of heart 14.

Lead migration detection module 120 may be configured to process the (near field) cardiac signal to detect the evoked response to the test stimulation signal. An example evoked response may take the form of a normal cardiac waveform (P-wave, QRS complex, and T-wave) that appears within a certain period of time following delivery of the stimulation pulse. Other examples of an evoked response may include a P-wave or a P-wave followed by some irregular waveform, an R-wave, or some other irregular amplitude peak. An example cardiac signal with an evoked response is show and described with respect to FIG. 8.

Lead migration detection module 120 may analyze the cardiac signal to detect an evoked response by, for example, measuring an amplitude of the cardiac signal and comparing the determined amplitude to a threshold value stored in memory 102. The amplitude may be, for example, a mean or median amplitude. In other examples, lead migration detection module 120 may detect an amplitude spike following the delivery of the test stimulation signal by signal generator 116. In yet other examples, lead migration detection module 120 may correlate the cardiac signal sensed following the delivery of the test stimulation signal with values stored in a memory 102 and compare the correlation value to a threshold value. The values may indicate, for example, a waveform of a sinus rhythm. For each example detection method, lead migration detection module 120 may analyze the cardiac signal over a period of time following delivery of the test stimulation signal. The period of time may be selected so as to substantially avoid detecting a normal cardiac waveform as an evoked response to the test stimulation delivered by neurostimulation module 106 to determine whether lead 28 has migrated from target tissue site 40.

In some examples, lead migration detection module 120 may determine whether electrodes 80-83 of neurostimulation lead 28 have migrated toward heart 14 based on a far field cardiac signal (e.g., an ECG or EGM) sensed by sensing module 118 of neurostimulation therapy module 106 via a subset of electrodes 80-83 of neurostimulation lead 28. Because the amplitude of the far field cardiac signal may decrease as the distance between heart 14 and neurostimulation electrodes 80-83 of lead 28 increases, lead migration detection module 120 may analyze the far field ECG or EGM signal to determine whether the position of lead 28 relative to heart 14 indicates the withholding of neurostimulation therapy or other adjustment to neurostimulation therapy is desirable. In one example, lead migration detection module 120 may analyze the far field cardiac signal by measuring an amplitude of the far field cardiac signal and comparing the amplitude to a threshold value stored in memory 102. The predetermined and stored threshold amplitude value may indicate the maximum amplitude value that indicates electrodes 80-83 are at least a predetermined distance from heart 14. The predetermined distance may be, for example, a minimum distance away from heart 14 at which the delivery of neurostimulation to patient 12 via electrodes 80-83 does not capture heart 14. Thus, if the determined amplitude value is greater than or equal to the threshold value, lead migration detection module 120 may control neurostimulation module 106 to suspend or otherwise adjust the delivery of neurostimulation to patient 12. In other examples, lead migration detection module 120 may determine the polarity, morphology, or frequency content of the ECG or EGM signal and selectively withhold delivery of neurostimulation to patient 12 based on a comparison of the determined value to a corresponding threshold value.

Additionally or alternatively, lead migration detection module 120 may analyze the far field cardiac signal by measuring a change in amplitude, polarity, morphology, or frequency content over time. As an example, lead migration detection module 120 may track the position of lead 28 relative to heart 14 based on the change in amplitude of the far field cardiac signal. A sudden change in amplitude of the far field cardiac signal, as indicated by an abrupt change in amplitude over time (e.g., a large slope) may indicate neurostimulation electrodes 80-83 of lead 28 have migrated toward heart 14. Thus, in some examples, if the change in amplitude over time is greater than or equal to a threshold slope value stored in memory 102, lead migration detection module 120 may control neurostimulation module 106 to suspend or otherwise adjust the delivery of neurostimulation to patient 12.

In an additional example, lead migration detection module 120 may analyze the far field cardiac signal by detecting the presence of one or both of a P-wave and an R-wave in the far field electrical cardiac signal. When lead 28 is located at target tissue site 40, the far field signal may include both a P-wave and an R-wave, and the ratio of the size of the P-wave to the R-wave may be used to determine a threshold value that indicates lead 28 is located at target tissue site 40. The size of the P-wave and R-wave may be determined by measuring an amplitude or by integrating the respective signal components. The ratio value may change when lead 28 migrates from target tissue site 40. For example, the ratio value may increase if lead 28 migrates into right atrium 30 (FIG. 1) and the ratio value may decrease if lead 28 migrates in right ventricle 32 (FIG. 1). Thus, lead migration detection module 120 may analyze the far field ECG or EGM signal to determine the ratio value and selectively withhold or otherwise adjust the delivery of neurostimulation to patient 12 based on the comparison of the ratio value to a threshold value or range of values. In particular, a range of values may be bounded by a maximum value and a minimum value. When the determined ratio value is greater than the maximum value or less than the minimum value, lead migration detection module 120 may withhold delivery or otherwise adjust the delivery of neurostimulation to patient 12.

In another example, IMD 16 may compare or correlate the far field cardiac signal with a near field cardiac signal sensed by sensing module 114 of cardiac therapy module 104 via a subset of electrodes 50, 52, 54, 56, 58, 60, 72, 74, and 76 of cardiac therapy leads 18, 20, 22. In this example, lead migration detection module 120 may compare an amplitude of the near field and far field cardiac signals or correlate a portion of the near field and far field cardiac signals with each other. The near field cardiac signal sensed by sensing module 114 of cardiac therapy module 104 may generally comprise a higher amplitude than the far field cardiac signal because of the proximity of cardiac therapy electrodes 50, 52, 54, 56, 58, 60, 72, 74, and 76 to heart 14.

When lead migration detection module 120 compares the near field and far field signals to determine whether neurostimulation electrodes 80-83 of lead 28 have migrated toward heart 14, the amplitude of the far field cardiac signal may be subtracted from the amplitude of the near field cardiac signal to determine a difference value. The difference amplitude value may be compared to a threshold amplitude value stored in memory 102 to determine whether the position of neurostimulation electrodes 80-83 relative to heart 14 indicates lead 28, and, therefore, neurostimulation electrodes 80-83 have migrated toward heart 14.

Similarly, lead migration detection module 120 may compare a correlation value for the near field and far field signals to a threshold value. The correlation value may indicate the extent to which the amplitudes of the near field and far field cardiac signals match. If the difference threshold value is less than the stored threshold value or the correlation value is higher than a correlation threshold value, lead migration detection module 120 may control neurostimulation module 120 to withhold or otherwise adjust the delivery of neurostimulation to patient 12.

Lead migration detection module 120 may also provide additional or alternative techniques to those described in the previous paragraphs, e.g., detecting loss of nerve and/or muscle capture, detecting cardiac capture, and analyzing far field cardiac signals, to detect migration of neurostimulation lead 28. For example, lead migration detection module 120 may determine an electrical parameter value indicative of an impedance of an electrical path between the electrodes of one or more of leads 18, 20, and 22 and one or more electrodes of lead 28 to detect migration of lead 28 from the implant site. For example, lead migration detection module 120 may control signal generator 112 of cardiac therapy module 104 to transmit an electrical signal across two or more electrodes of leads 18, 20, and 22 and 80-83 and sensing module 118 may sense the electrical signal via one or more electrodes of lead 28. In some examples, housing electrode 68 may also be used to determine the impedance. The electrical signal may provide therapeutic benefits to patient 12 or may not provide therapeutic benefits to patient 12. IMD 16 may utilize a bipolar, tripolar, or quadrapolar electrode configuration to determine the impedance of an electrical path between one or more electrodes of cardiac leads 18, 20, and 22 and one or more electrodes of neurostimulation lead 28.

In examples in which lead migration detection module 120 uses a quadrapolar configuration to determine the impedance between one or more cardiac therapy electrodes 50, 52, 54, 56, 58, 60, 72, 74, and 76 and one or more neurostimulation therapy electrodes 80-83, signal generator 112 of cardiac therapy module 104 may transmit an electrical signal across two electrodes 50, 52, 54, 56, 58, 60, 72, 74, and 76 of leads 18, 20, and 22 and sensing module 118 of neurostimulation therapy module 106 may sense the electrical signal using two electrodes 80-83 of lead 28. Because cardiac leads 18, 20, and 22 and neurostimulation lead 28 are implanted at separate locations within the body of patient 12, neurostimulation therapy module 106 may sense and electrical signal that has transmitted across an electrical path between the electrodes of cardiac lead(s) and the electrodes neurostimulation lead. In this way, lead migration detection module 120 may determine the resulting voltage or current of the sensed signal and use the determined value to determine an impedance value.

In other examples, signal generator 116 of neurostimulation therapy module 106 may transmit an electrical signal using two or more neurostimulation electrodes 80-83 of lead 28 and sensing module 114 of cardiac therapy module 104 may sense the electrical signal via electrodes of leads 18, 20, 22. In either example, lead migration detection module 120 may compare the determined impedance value to a threshold impedance value stored in memory 102 to determine whether lead 28 have migrated. The determined impedance value may indicate whether electrodes 80-83 of lead 28 have migrated towards heart 14. As electrodes 80-83 of lead 28 move closer to heart 14, the distance between electrodes 80-83 of lead 28 and electrodes 50, 52, 54, 56, 58, 60, 72, 74, and 76 of leads 18, 20, 22 and housing electrode 68 may decrease. Accordingly, as electrodes 80-83 of lead 28 move closer to heart 14, an impedance of the electrical path between electrodes 80-83 of lead 28 and electrodes 50, 52, 54, 56, 58, 60, 72, 74, and 76 of leads 18, 20, 22 and housing electrode 68 may decrease. Thus, lead migration detection module 120 may determine that electrodes 80-83 of lead 28 have migrated towards heart 14 if the determined impedance value of the electrical path between electrodes 80-83 of lead 28 and electrodes 50, 52, 54, 56, 58, 60, 72, 74, and 76 of leads 18, 20, 22 and housing electrode 68 is less than the threshold impedance value. If the determined impedance value is less than the stored threshold impedance value, lead migration detection module 120 may control neurostimulation therapy module 120 to withhold the delivery of neurostimulation to patient 12.

In general, lead migration detection module 120 may control neurostimulation therapy module 106 to suspend or otherwise adjust the delivery of neurostimulation to patient 12 using any suitable technique. While suspension of neurostimulation is primarily referred to herein, lead migration detection module 120 may also control neurostimulation therapy module 106 to modify one or more neurostimulation parameter values, such as an amplitude, frequency, pulse width, duty cycle, and the like. Thus, the techniques described herein that relate to suspension of neurostimulation therapy may also apply to the adjustment of one or more neurostimulation parameters and the delivery of neurostimulation according to the adjusted neurostimulation parameters.

In some examples, in order to suspend the delivery of neurostimulation, lead migration detection module 120 may generate an interference indication that indicates that lead 28 has migrated within patient 12 and that further delivery of neurostimulation to patient 12 via electrodes 80-83 of lead 28 may be undesirable. Based on the generation of the interference indication, neurostimulation therapy module 106 may withhold any further generation of neurostimulation until user input is received, e.g., resetting the interference indication. Processor 100 of IMD 16 may transmit the interference indication to programmer 24 to alert a user that lead 28 may have migrated and/or that neurostimulation therapy has been suspended and medical attention is recommended. Programmer 24 may display a visual message (e.g., text or graphics), audible message or somatosensory alert that indicates neurostimulation has been suspended and, in some examples, additional information, such as a code that provides information about the suspension. Lead migration detection module 120 may alternatively or additionally cause IMD 16 to generate an alert that may be detected by patient 12. The alert may be an audible alert, such as a beeping sound, or a somatosensory alert, such as a vibration emitted by IMD 16.

Following the suspension of neurostimulation therapy, programmer 24 send a signal to IMD 16 that causes IMD 16 to revert back to executing therapy programs that include neurostimulation. For example, a user (e.g., patient 12 or clinician) may provide input to programmer 24 in order to instruct IMD 16 to revert back to executing therapy programs that include neurostimulation. In some examples, IMD 16 may also automatically revert back to executing a therapy program that includes neurostimulation when IMD 16 determines that delivering neurostimulation therapy to patient 12 will not be likely to capture heart 14 or interfere with the sensing of electrical cardiac signals and/or delivery of therapy by cardiac therapy module 104. In other examples, a clinician may interact with programmer 24 to restart the delivery of neurostimulation to patient 12 via neurostimulation therapy module 106, e.g., after evaluating the position of lead 28 and/or repositioning lead 28. The clinician may evaluate the position of lead 28 by, for example, any suitable medical imaging technique, such as fluoroscopy, x-ray imaging, MRI, or ultrasound imaging, to determine the location of lead 28. Lead 28 may include a radiographic marker for identification purposes during an imaging procedure.

Figure 5:
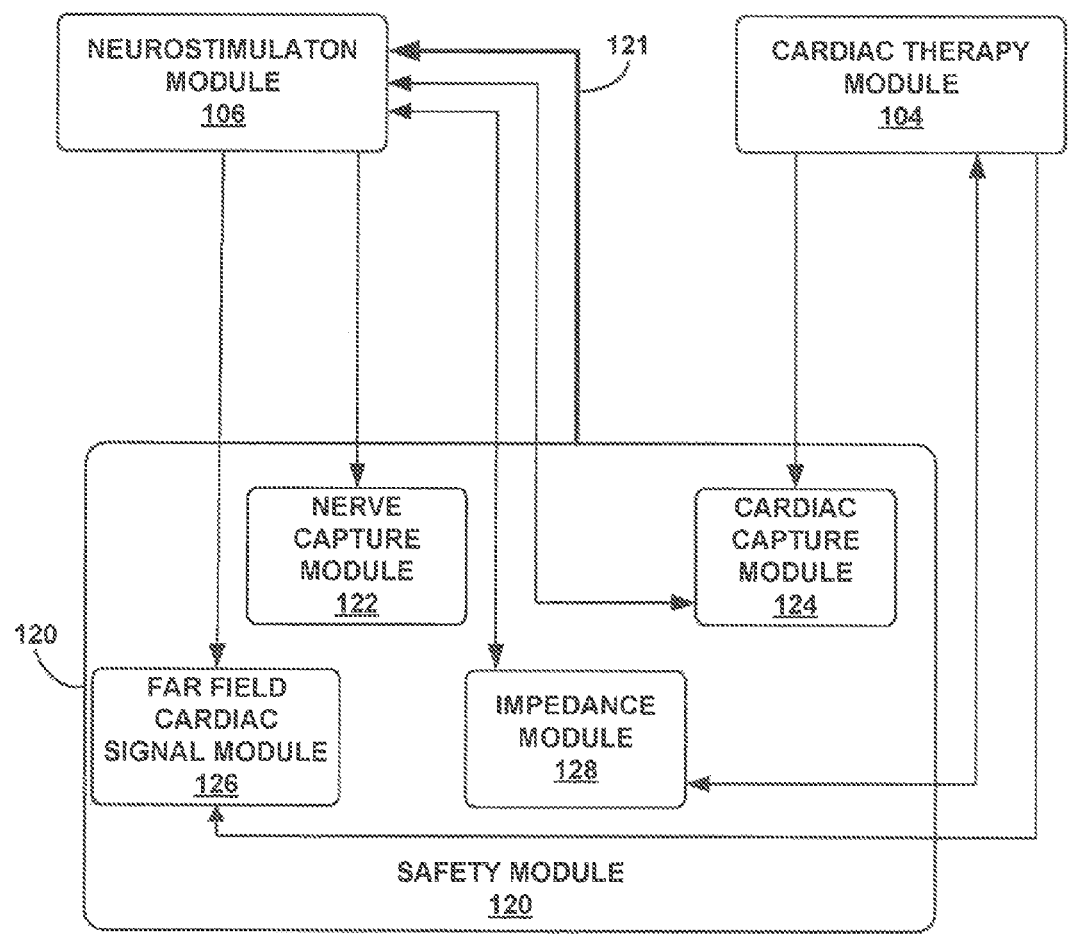
FIG. 5 is a function block diagram of the lead migration detection module shown in FIG. 4.

FIG. 5 is a functional block diagram illustrating lead migration detection module 120 of IMD 16 in greater detail. In the example illustrated in FIG. 5, lead migration detection module 120 includes nerve capture module 122, cardiac capture module 124, far field cardiac signal module 126, and impedance module 128. Although FIG. 5 illustrates lead migration detection module 120 as including each of the modules, in other examples lead migration detection module 120 may include any number of the modules. In general, the purpose of FIG. 5 is to illustrate a logical relationship between the various features provided by lead migration detection module 120 and the cardiac therapy and neurostimulation modules 104 and 106, respectively.

In the illustrated example of FIG. 5, a signal path 121 is shown. Lead migration detection module 120 may use signal path 121 to transmit information to neurostimulation module 106. For example, lead migration detection module 120 may transmit a control signal to neurostimulation module 106 via signal path 121, where the signal may control neurostimulation module 106 to withhold or otherwise adjust the generation and delivery of neurostimulation to patient 12. Thus, when any of modules 122, 124, 126, or 128 determine that delivery of neurostimulation to patient 12 is undesirable, the respective module 122, 124, 126, or 128 may send a control signal to neurostimulation module 106 via signal path 121. The modules 122, 124, 126, or 128 may determine that neurostimulation is undesirable, for example, because movement of lead 28 has been detected, which may indicate that electrodes 80-83 have moved closer to heart 14.

In accordance with the description provided in FIG. 4, nerve capture module 122 may analyze an electrical signal received from neurostimulation therapy module 106, such as an electrical nerve signal (e.g., an ENG) or an electrical muscle signal (e.g., EMG), to detect a physiological response to a stimulation signal delivered to patient 12 via electrodes 80-83 of lead 28. Cardiac capture module 124 may analyze a cardiac signal sensed via at least some of electrodes 80-83 (not shown in FIG. 5) electrically connected to neurostimulation therapy module 106 to detect a physiological response to a stimulation signal delivered to patient 12 via electrodes 80-83 of lead 28.

FIG. 5 shows signal paths for neurostimulation module 104 and cardiac therapy module 106 to transmit a far field cardiac signal and near field cardiac signal, respectively, to far field cardiac signal module 126. Far field cardiac signal module 126 may receive a cardiac signal sensed via sensing module 118 of neurostimulation therapy module 106, which may be referred to as the far field cardiac signal because of the relative proximity of electrodes 80-83 with which sensing module 118 may sense the cardiac signal to heart 14 (e.g., compared to electrodes 50, 52, 54, 56, 58, 60, 72, 74, and 76 electrically connected to cardiac therapy module 104). Far field cardiac signal module 126 may analyze the far field cardiac signal using the techniques described above to determine the position of lead 28 relative to heart 14. For example, far field cardiac signal module 126 may determine an amplitude of the far field cardiac signal and compare it to a stored threshold amplitude value, or compare or correlate the far field cardiac signal with a near field cardiac signal. The near field cardiac signal may be a cardiac signal sensed by sensing module 114 (FIG. 4) of cardiac therapy module 104, which may be referred to as "near field" signal because of the relative proximity of electrodes 50, 52, 54, 56, 58, 60, 72, 74, and 76 with which sensing module 114 may sense to the cardiac signal to heart 14.

Impedance module 128 may monitor an impedance between electrodes of one or more of leads 18, 20, and 22 connected to cardiac therapy module 104 and electrodes of lead 28 connected to neurostimulation module 106. In particular, impedance module 128 may communicate with neurostimulation therapy module 106 to transmit an electrical signal and communicate with cardiac therapy module 104 receive the sensed signal. Alternatively, impedance module 128 may communicate with cardiac therapy module 104 to transmit an electrical signal and communicate with neurostimulation therapy module 106 to receive the sensed signal. As previously described, impedance module 128 may determine an electrical parameter value indicative of an impedance of an electrical path between electrodes of one or more of leads 18, 20, and 22 and electrodes of lead 28. The electrical parameter may be, for example, a current or voltage amplitude of the sensed signal. Based on the an electrical parameter, impedance module 128 may send a control signal to neurostimulation therapy module 106 via signal path 121 to selectively withhold delivery of neurostimulation to patient 12.

Figure 6:
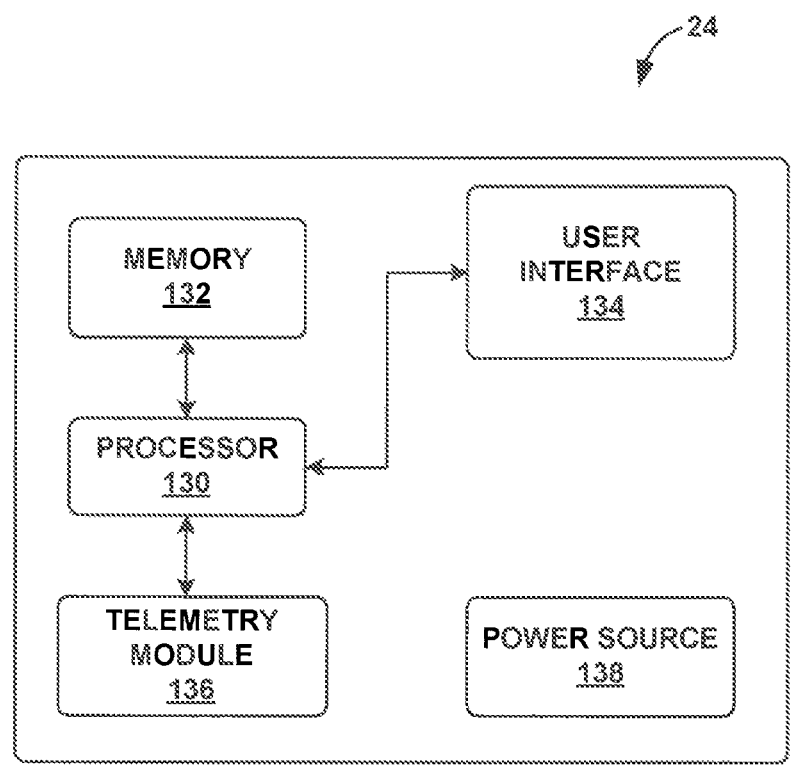
FIG. 6 is a functional block diagram of an exemplary medical device programmer.

FIG. 6 is block diagram of an example programmer 24. As shown in FIG. 6, programmer 24 includes processor 130, memory 132, user interface 134, telemetry module 136, and power source 138. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to IMD 16 (FIG. 1). The therapy programs may be for either or both cardiac therapy module 104 and neurostimulation module 106 (FIG. 4). The clinician may interact with programmer 24 via user interface 134, which may include display to present graphical user interface to a user, and a keypad or another mechanism for receiving input from a user.

Processor 130 can take the form one or more microprocessors, DSPs, ASICs, FPGAs, programmable logic circuitry, or the like, and the functions attributed to processor 130 herein may be embodied as hardware, firmware, software or any combination thereof. Memory 312 may store instructions that cause processor 130 to provide the functionality ascribed to programmer 24 herein, and information used by processor 130 to provide the functionality ascribed to programmer 24 herein. Memory 132 may include any fixed or removable magnetic, optical, or electrical media, such as RAM, ROM, CD-ROM, hard or floppy magnetic disks, EEPROM, or the like. Memory 132 may also include a removable memory portion that may be used to provide memory updates or increases in memory capacities. A removable memory may also allow patient data to be easily transferred to another computing device, or to be removed before programmer 24 is used to program therapy for another patient. Memory 132 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 136, which may be coupled to an internal antenna or an external antenna. An external antenna that is coupled to programmer 24 may correspond to the programming head that may be placed proximate to the patient's body near the IMD 16 implant site, as described above with reference to FIG. 1. Telemetry module 136 may be similar to telemetry module 108 of IMD 16 (FIG. 4).

Telemetry module 136 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection.

Power source 138 delivers operating power to the components of programmer 24. Power source 138 may include a battery and a power generation circuit to produce the operating power. In some examples, the battery may be rechargeable to allow extended operation. Recharging may be accomplished by electrically coupling power source 138 to a cradle or plug that is connected to an alternating current (AC) outlet. In addition or alternatively, recharging may be accomplished through proximal inductive interaction between an external charger and an inductive charging coil within programmer 24. In other examples, traditional batteries (e.g., nickel cadmium or lithium ion batteries) may be used. In addition, programmer 24 may be directly coupled to an alternating current outlet to power programmer 24. Power source 138 may include circuitry to monitor power remaining within a battery. In this manner, user interface 134 may provide a current battery level indicator or low battery level indicator when the battery needs to be replaced or recharged. In some cases, power source 138 may be capable of estimating the remaining time of operation using the current battery.

Figure 7:
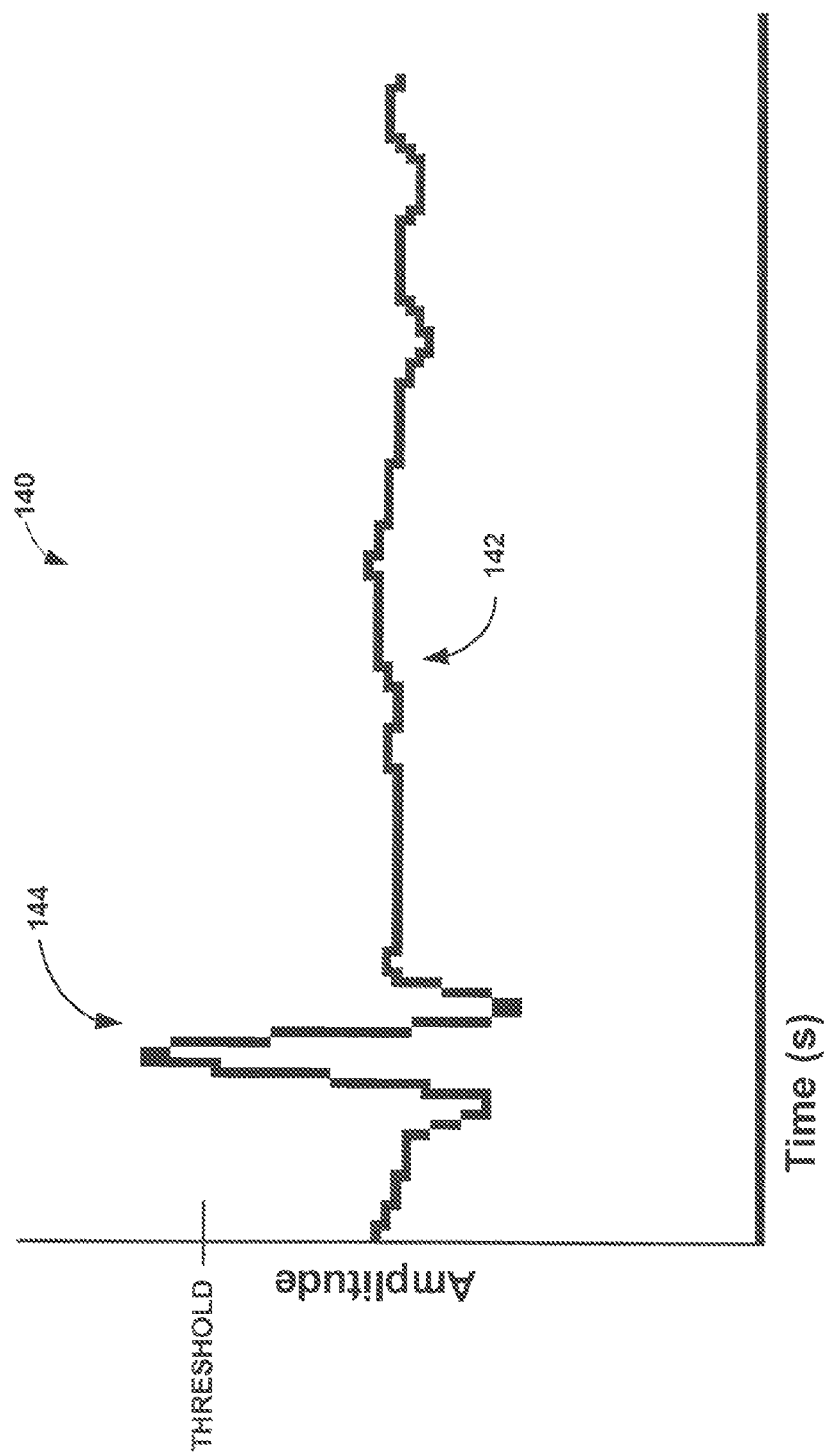
FIG. 7 illustrates an exemplary electrical nerve signal that includes a response to a neurostimulation signal.

FIG. 7 illustrates a conceptual illustration of electrical nerve signal 140 that may be generated by a target nerve in response to the delivery of neurostimulation therapy by neurostimulation therapy module 106 (FIG. 4) of IMD 16. Sensing module 118 (FIG. 4) of neurostimulation therapy module 106 may generate electrical nerve signal 140 in response to sensed nerve activity. In the example shown in FIG. 7, the target nerve may be a vagus nerve of patient 12. Electrical nerve signal 140 includes a baseline component 142 and a response component 144. Baseline component 142 represents normal activity of the vagus nerve, e.g., activity without the delivery of neurostimulation by neurostimulation therapy module 106. The vagus nerve generates a response, as indicated by response component 144, in response to the delivery of a stimulation signal to target tissue site 40 by signal generator 116 (FIG. 4) of neurostimulation module 106.

In the example shown in FIG. 7, response component 144 comprises an amplitude that is greater than or equal to a threshold amplitude value (as indicated by THRESHOLD in FIG. 7), which indicates that there is no loss of nerve capture. In other words, stimulation delivered by neurostimulation module 106 captures the vagus nerve, as indicated by the amplitude of response component 144 of electrical nerve signal 140. The presence of nerve capture may indicate that electrodes 80-83 of lead 28 (FIG. 2) are positioned to deliver stimulation to target tissue site 40 (FIG. 1) and have not migrated away from target tissue site 40 and, for example, towards heart 14. As previously described, IMD 16 may continue to deliver neurostimulation to patient 12 when electrical signal 144 exhibits response component 144 of a sufficient amplitude in response to the delivery of neurostimulation by neurostimulation therapy module 106 because response component 144 indicates that lead 28 is positioned close enough to original implant site. This may indicate that the delivery of neurostimulation is not likely to capture heart 14.

Figure 8:
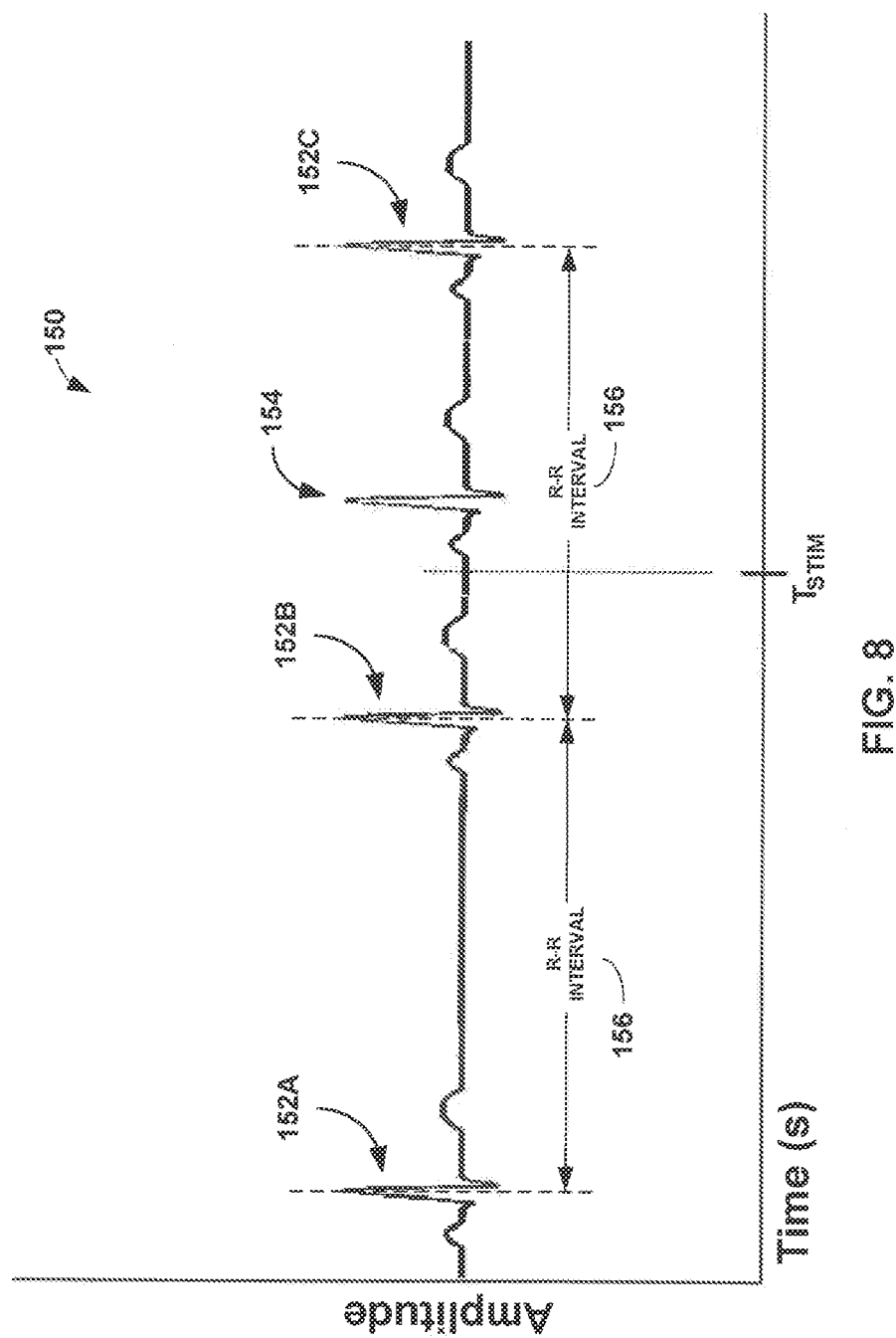
FIG. 8 illustrates an exemplary electrical cardiac signal that includes an evoked response to the delivery of a neurostimulation signal.

FIG. 8 illustrates an example cardiac signal 150 that may be generated by sensing module 114 (FIG. 4) of cardiac therapy module 106 of IMD 16 via electrically activity sensed by any combination of electrodes 50, 52, 54, 56, 58, 60, 68, 72, 74, and 76 electrically connected to cardiac therapy module 104 or via electrical activity sensed via electrodes 68, 80-83 electrically connected to neurostimulation therapy module 106. In FIG. 8, cardiac signal 150 may comprise an ECG or EGM signal. In FIG. 8, signal 150 includes a baseline cardiac rhythm that includes baseline cardiac waveforms 152A-152O (hereinafter referred to as "baseline cardiac waveforms 152") that indicate a normal sinus rhythm of heart 14, and an evoked response 154.

Cardiac signal 150 is sensed over a period of time that includes the time in which stimulation module 116 (FIG. 4) of neurostimulation module 106 generates and delivers an electrical stimulation signal, e.g., a test stimulation signal, to target tissue site 40 via a selected combination of electrodes 80-83 of neurostimulation lead 28 (FIG. 4). IMD 16 delivers the test stimulation signal to target tissue site 40 at time $T_{STIM}$. As shown in FIG. 8, cardiac signal 150 exhibits evoked response 154 shortly after neurostimulation therapy module 106 delivers the test stimulation signal via two or more electrodes 80-83 of lead 28 at time $T_{STIM}$. For example, if the test stimulation signal captures right atrium 30, the evoked response may be a P-wave within approximately 40 milliseconds (ms) of delivering of the test signal, although other time ranges are contemplated. In this example, an R-wave may follow the P-wave within approximately 250 ms, although other time ranges are contemplated. In these examples, IMD 16 may deliver the test signal when the AV node is not in refractory. If, however, IMD 16 delivers the test signal when the AV node is in refractory the evoked response may be only a P-wave located within approximately 40 ms of delivery of the test signal. In this case, an R-wave may not follow the P-wave since the AV node is in refractory. In an example in which the test signal captures right ventricle 32, the evoked response may be an R-wave within approximately 40 ms of delivery of the test signal with no subsequent P-wave.

Cardiac capture module 124 (FIG. 5) of lead migration detection module 120 (FIG. 4) of IMD 16 may analyze electrical cardiac signal 150 over a window of time following time $T_{STIM}$. In some examples, neurostimulation therapy module 106 delivers the electrical stimulation signal at a time between normal baseline cardiac waveforms, and cardiac capture module 124 analyzes the cardiac signal 150 over a window of time following delivery of the electrical stimulation signal for an evoked response by heart 14.

As FIG. 8 illustrates, prior to the delivery of the neurostimulation signal, the R-waves of each of the baseline cardiac waveforms 152 are substantially evenly spaced by R-R interval 156. Because evoked response 154 occurs after baseline cardiac rhythm 152B, but within a shorter amount of time following an immediately preceding R-wave than R-R interval 156, cardiac capture module 124 may determine that evoked response 154 was in fact a response to the delivery of the neurostimulation signal, rather than a normal cardiac rhythm of patient 12. Cardiac capture module 124 may determine that because evoked response 154 was detected following time $T_{STIM}$, the neurostimulation signal captured heart 14, thereby indicating that lead 28 may have migrated toward heart 14.

Cardiac capture module 124 may, in one example, compare an amplitude of cardiac signal 150 after time $T_{STIM}$ to a threshold value, and detect evoked response 154 when the amplitude of cardiac signal 150 is greater than the threshold value. The threshold value may be an amplitude value of a typical R-wave for P-wave for the patient's cardiac rhythm. Other techniques for detecting an evoked response are contemplated. It is recognized that the detection method may vary based on the type of evoked response that can be expected as a result of a neurostimulation pulse. In the example shown in FIG. 8, evoked response 154 is a cardiac waveform similar to baseline cardiac waveforms 152, but may take other forms. Other examples of an evoked response include a distorted variation of a normal sinus rhythm such as a P-wave, an R-wave, or other waveform of a sinus rhythm that is not synchronized with the normal sinus rhythm of patient 12.

FIGS. 9-12 are flow diagrams of example techniques for selectively controlling neurostimulation therapy to patient 12 upon determining that neurostimulation lead 28 may have moved such that electrodes 80-83 of lead 28 have migrated towards heart 14.

Figure 9:
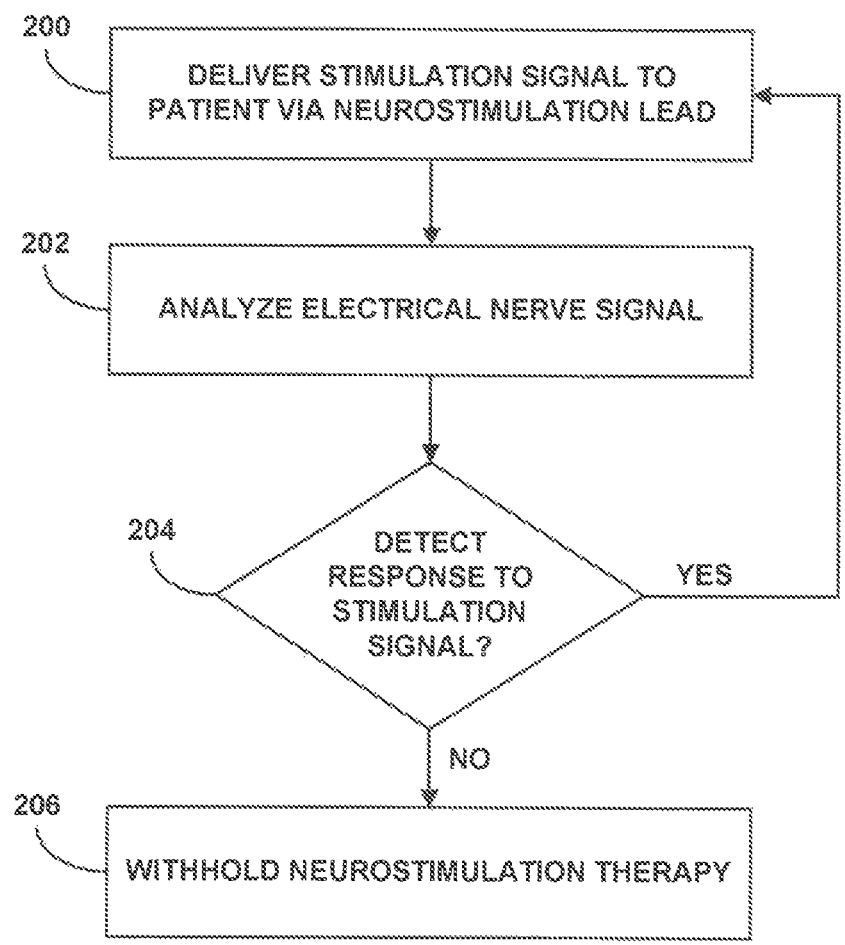
FIGS. 9-12 are flow diagrams illustrating exemplary techniques for selectively withholding delivery of neurostimulation therapy to a patient based on a determination that one or more neurostimulation leads may have migrated toward the patient's heart.

FIG. 9 is a flow diagram of an example technique for selectively withholding delivery of neurostimulation therapy to patient 12 based on detecting a loss of nerve capture with electrodes of neurostimulation lead 28 (FIG. 4). IMD 16 may deliver an electrical stimulation signal to patient 12 (200). As previously described, signal generator 116 of neurostimulation module 106 may generate a test stimulation signal and deliver the test stimulation signal to target tissue site 40 (FIG. 1) via one or more of electrodes 80-83 of lead 28. The stimulation signal may comprise, for example, a pulse waveform having a frequency of about 1 Hz and an amplitude of about 8 V. In some examples, the stimulation signal is not configured to provide neurostimulation therapy, e.g., therapeutic benefits to patient 12. Rather, the stimulation signal may be configured to trigger a physiological response from the target nerve or tissue proximate to the vagus nerve, such as laryngeal muscle tissue or other muscle tissue. However, in some examples, the test stimulation signal may be configured to provide neurostimulation therapy to patient 12.

After the test stimulation signal is delivered to patient 12 via neurostimulation lead 28 (200), sensing module 118 (FIG. 4) of neurostimulation therapy module 106 may sense an electrical nerve signal, e.g., via a subset of electrodes 80-83 of lead 28. Nerve capture module 122 (FIG. 4) of lead migration detection module 120 (FIG. 4) of IMD 16 may analyze the electrical nerve signal (202) to determine whether the delivery of the test stimulation signal resulted in a physiological response (204). That is, nerve capture module 122 may analyze the electrical nerve signal to determine if the stimulation signal captured the target nerve (e.g., the vagus nerve). An example electrical nerve signal is shown in FIG. 7.

In other examples, nerve capture module 122 also analyzes an electrical signal that is indicative of other physiological responses, such as muscle movement, to the delivery of the test stimulation signal, as previously described. Nerve capture module 122 may analyze the electrical nerve signal to determine whether the nerve was captured by, for example, comparing an amplitude of the electrical nerve signal to a predetermined threshold amplitude value stored in memory 102 (FIG. 4) of IMD 16. In particular, nerve capture module 122 may analyze a portion of the electrical nerve signal that corresponds to a time interval following delivery of the test stimulation signal by neurostimulation therapy module 106.

If nerve capture module 122 detects a response to the stimulation signal, processor 100 may determine that electrodes 80-83 of lead 28 have not migrated away from target tissue site 40. Thus, if nerve capture module 122 detects a response to the stimulation signal, i.e., nerve capture, IMD 16 may continue to periodically perform technique shown in FIG. 9. For example, IMD 16 may repeat the steps of FIG. 9 on a weekly basis, a daily basis, an hourly basis, or several times per day.

If, however, nerve capture module 122 does not detect a response to the stimulation signal, processor 100 may determine lead 28 has moved such that there is a loss of nerve capture by the neurostimulation. Processor 100 may control neurostimulation therapy module 106 to withhold the delivery of neurostimulation to patient 12 (206). Loss of nerve capture may indicate that lead 28 has migrated from the target tissue site 40. Because there is a possibility that lead 28 may have migrated to a position where neurostimulation therapy may be coupled to heart 14, IMD 16 may withhold delivery of neurostimulation therapy.

As previously described, IMD 16 may take further action after detecting a loss of nerve capture. For example, IMD 16 may communicate with programmer 24 to provide an alert to patient 12 (or patient caretaker) or a clinician that there is a loss of nerve capture. Additionally or alternatively, IMD 16 may generate an alert, such as a beeping sound or a vibrational pattern, to indicate the loss of nerve capture. A clinician may then use imaging procedures to determine the position of lead 28 and take action based on the position of lead 28.

Figure 10:
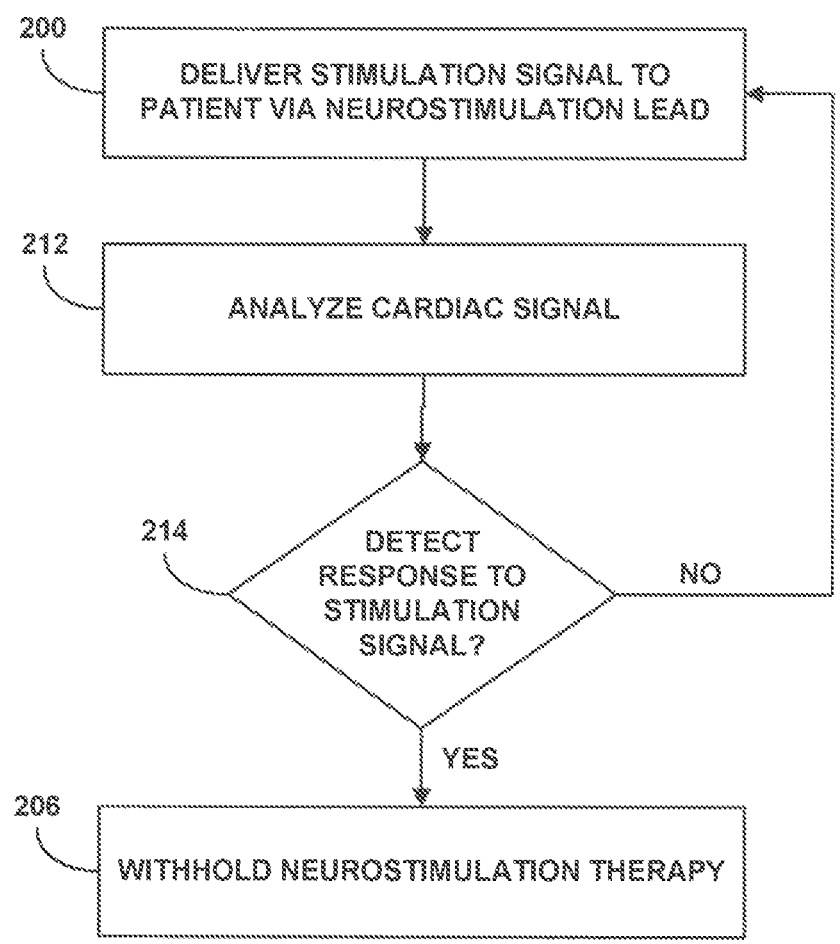

FIG. 10 is a flow diagram of an example technique for selectively withholding delivery of neurostimulation therapy to patient 12 based on the detection of cardiac capture by stimulation delivered via a neurostimulation signal. Signal generator 116 of neurostimulation therapy module 106 (FIG. 4) may deliver a test stimulation signal to patient 12 (200). Either sensing module 114 of cardiac therapy module 104 (FIG. 4) or sensing module 118 of neurostimulation therapy module 106 (FIG. 4) may sense a cardiac signal (e.g., an EGM or ECG signal) following the delivery of the test stimulation signal. Cardiac capture module 124 (FIG. 5) of lead migration detection module 120 (FIG. 4) of IMD 16 may analyze the sensed cardiac signal (212) to detect a response to the test stimulation (214). In particular, cardiac capture module 124 may analyze the sensed cardiac signal to determine if the stimulation resulted in cardiac capture, e.g., whether the test stimulation evoked a response by heart 14. Cardiac capture may result from the delivery of the test stimulation via electrodes of neurostimulation lead 28 if electrodes 80-83 of neurostimulation lead 28 have migrated within a particular distance range of heart 14.

In some examples, cardiac capture module 124 may determine whether the test stimulation signal captured heart 14, e.g., whether electrodes 80-83 of neurostimulation lead 28 have migrated within the particular range of heart 14, by comparing an amplitude of the sensed cardiac signal to a predetermined threshold amplitude value stored in memory 102 (FIG. 4) of IMD 16. In particular, cardiac capture module 124 may analyze a portion of the electrical cardiac signal that corresponds to a time interval following delivery of the stimulation signal. An example cardiac signal is shown in FIG. 8.

If cardiac capture module 124 does not detect a physiological response to the stimulation signal, IMD 16 may continue to periodically repeat technique shown in FIG. 10. For example, IMD 16 may repeat the steps of FIG. 10 on a weekly basis, a daily basis, an hourly basis, or several times per day. If, however, cardiac capture module 124 detects an evoked cardiac response to the test stimulation signal, processor 100 may determine the test stimulation signal captured heart 14. Processor 100 may then control neurostimulation therapy module 106 to withhold the delivery of neurostimulation to patient 12 (206). Cardiac capture may indicate that lead 28 has migrated from target tissue site 40. Consequently, IMD 16 may suspend the delivery of neurostimulation therapy.

As previously described with respect to the example method shown in FIG. 9, IMD 16 may take further action after detecting a loss of nerve capture. For example, IMD 16 may generate an alert to warn patient 12 or a clinician that neurostimulation therapy has been suspended, e.g., by communicating with programmer 24 or by emitting an audible alert or vibrations.

Figure 11:
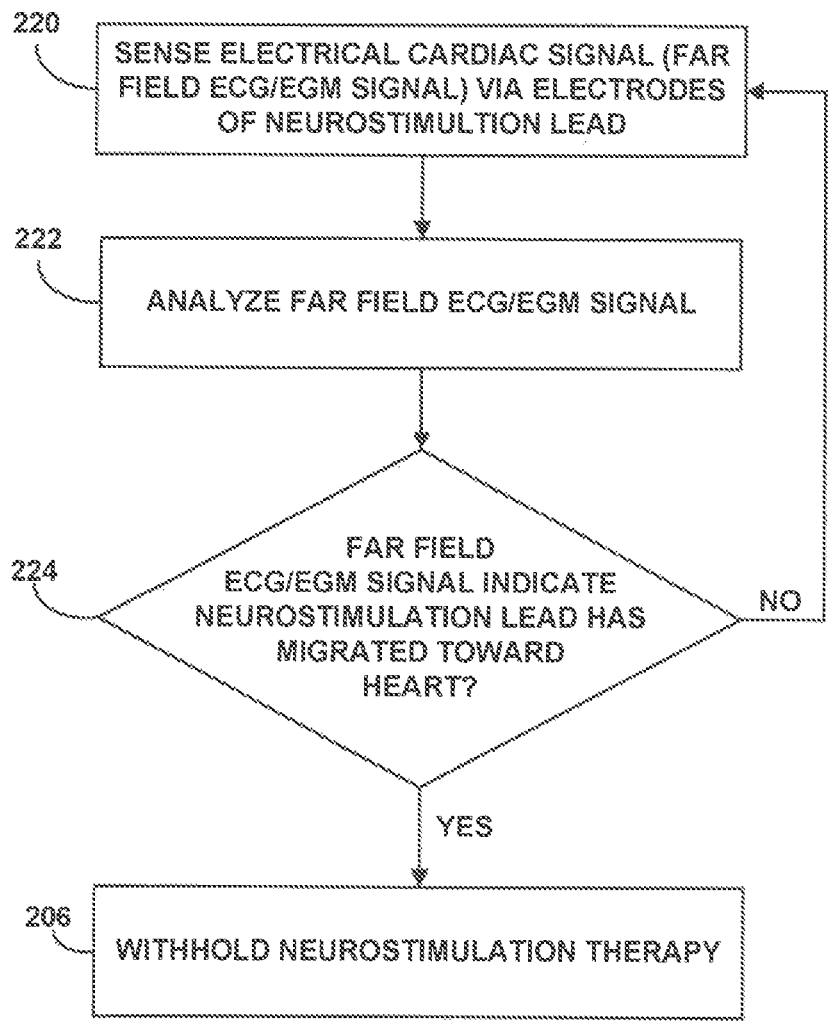

FIG. 11 is a flow diagram of an exemplary technique for selectively withholding delivery of neurostimulation therapy to patient 12 based on a far field cardiac signal, which may be, for example, an EGM or an ECG sensed via two or more electrodes 80-83 (FIG. 4) electrically connected to neurostimulation therapy module 106. The far field cardiac signal may indicate the position of lead 28 relative to heart 14, which may be used to control the delivery of neurostimulation therapy to patient 12.

In accordance with the technique shown in FIG. 11, IMD 16 may sense electrical cardiac signals via one or more of electrodes 80-83 of neurostimulation lead 28 (220). In particular, sensing module 118 (FIG. 4) of neurostimulation module 106 may sense the cardiac signals and generate the far field cardiac signal. Far field cardiac signal module 126 (FIG. 5) of lead migration detection module 120 (FIG. 4) may analyze the far field ECG or EGM signal (222) to determine the position of electrodes 80-83 of neurostimulation lead 28 relative to heart 14. As one example, far field cardiac signal module 126 (FIG. 5) may compare an amplitude, or other signal characteristic, such as a polarity, morphology, or frequency content, of the far field cardiac signal to a predetermined threshold value.

In another example, far field cardiac signal module 126 may also analyze the far field ECG or EGM signal to determine a ratio of the size of a P-wave and an R-wave. As another example, far field cardiac signal module 126 may analyze the far field ECG or EGM signal by comparing the far field signal to a corresponding near field signal. In any case, far field cardiac signal module 126 determines the position of lead 28 relative to heart 14 based on the comparison (224). With respect to the example in which far field cardiac signal module 126 analyzes the amplitude of the far field signal, the amplitude of the far field cardiac signal may be a mean or median amplitude over a predetermined period of time or a change in amplitude of the cardiac signal over time (e.g., a slope). If the amplitude of the far field cardiac signal sensed via the neurostimulation electrodes 80-83 is not greater than a stored threshold value, far field cardiac signal module 126 may determine that neurostimulation electrodes 80-83 have not moved within a threshold distance away from target tissue site 40 and toward heart 14 (224) and IMD 16 may continue to deliver neurostimulation to patient 12. The threshold distance can be, for example, a distance away from target tissue site 40 that indicates electrodes 80-83 have migrated a sufficient distance toward heart 14 such that stimulation delivered via electrodes 80-83 may capture heart 14.

As discussed above, an overall amplitude of the far field cardiac signal may increase as the neurostimulation electrodes 80-83 move closer to heart 14. Accordingly, if the amplitude of the far field cardiac signal sensed via the neurostimulation electrodes 80-83 is greater or equal to a stored threshold value, far field cardiac signal module 126 may determine that neurostimulation electrodes 80-83 have migrated towards heart 14. Accordingly, far field cardiac signal module may control neurostimulation therapy module 106 to withhold the delivery of neurostimulation to patient 12 (206). Far field cardiac signal module 126 may also generate an interference indication that is transmitted to programmer 24 and/or generate an alert to notify patient 12 that neurostimulation therapy has been suspended.

Figure 12:
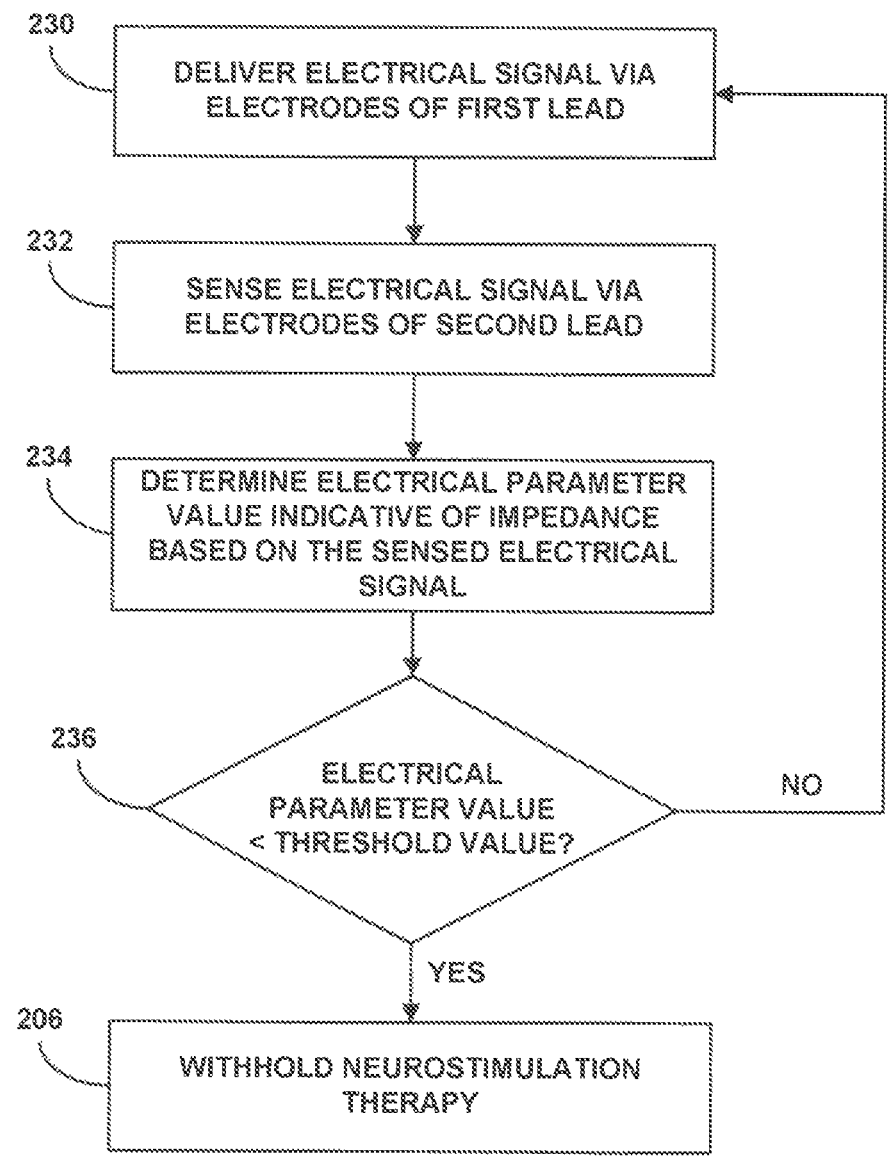

FIG. 12 is a flow diagram illustrating an example technique for selectively withholding neurostimulation therapy to patient 12 based on an impedance of an electrical path between electrodes 50, 52, 54, 56, 58, 60, 68, 72, 74, and 76 electrically connected to cardiac therapy module 104 (FIG. 4) and electrodes 68, 80, 81, 82 and/or 83 electrically connected to neurostimulation therapy module 106 (FIG. 4). IMD 16 may generate and deliver an electrical signal from electrodes of a first lead (230) and sense the electrical signal with electrodes of a second lead (232). In one example, the first lead may be a neurostimulation lead, e.g., lead 28, and the second lead may be a cardiac lead, such as one of leads 18, 20, and 22. In such an example, signal generator 116 (FIG. 4) of neurostimulation module 106 may generate the electrical signal and sensing module 114 (FIG. 4) of cardiac therapy module 104 may sense the electrical signal. In another example, the first lead may be a cardiac lead, such as one of leads 18, 20, and 22, and the second lead may be a neurostimulation lead, e.g., lead 28. In such an example, signal generator 112 (FIG. 4) of cardiac therapy module 104 may generate the electrical signal and sensing module 118 (FIG. 4) of neurostimulation module 106 may sense the electrical signal. The electrical signal used to determine impedance may not be configured to provide therapeutic benefits to patient 12. That is, the electrical signal may be configured such that it does not activate tissue, e.g., a nerve or muscle, and thus, does not provide a therapeutic benefit to patient 12. However, in some examples, the electrical signal delivered to determine the impedance of the electrical path may provide therapeutic benefits to patient 12.

Based on the sensed electrical signal and the known characteristics of the delivered electrical signal, impedance module 128 (FIG. 5) of lead migration detection module 120 (FIG. 4) of IMD 16 may determine an electrical parameter value indicative of an impedance of the electrical path between the electrodes of the first lead and the electrodes of the second lead (234). For example, impedance module 128 may determine a current amplitude of the sensed electrical signal, which may be indicative of the impedance of the electrical path if the voltage amplitude of the electrical signal delivered via the first lead is known. As another example, impedance module 128 may determine a voltage amplitude of the sensed electrical signal, which may be indicative of the impedance of the electrical path if the current amplitude of the electrical signal delivered via the first lead is known.

Impedance module 128 may compare the electrical parameter value indicative of impedance to a predetermined threshold value (236). Changes in an impedance of the electrical path between the electrodes of the first and second leads may indicate that one of the leads has moved. As previously described, movement of lead 28 towards leads 18, 20, 22 may be undesirable because movement of lead 28 toward leads 18, 20, 22 may indicate electrodes 80-83 of lead 28 have moved toward heart 14. Movement of electrodes 80-83 proximate to heart 14 may be undesirable because of the possibility that the neurostimulation signals generated by signal generator 116 of neurostimulation therapy module 106 may inadvertently capture heart 14. Movement of lead 28 toward heart 14 may also decrease the efficacy of the neurostimulation therapy because of the movement away from the target nerve.

If the electrical parameter value indicative of impedance of the electrical path between electrodes of lead 28 and electrodes of one or more of leads 18, 20, 22 has not abruptly changed, impedance module 128 may determine that the position of lead 28 relative to heart 14 is acceptable and indicates lead 28 has not migrated from target tissue site 40. IMD 16 may continue to periodically implement technique shown in FIG. 12. For example, IMD 16 may repeat the steps of FIG. 12 on a weekly basis, a daily basis, an hourly basis, or several times per day. If, however, the electrical parameter value indicative of impedance of the electrical path between electrodes of lead 28 and electrodes of one or more of leads 18, 20, 22 is less than the stored threshold value, processor 100 of IMD 16 may control neurostimulation therapy module 106 to withhold the delivery of neurostimulation to patient 12 (206). Processor 100 may also generate an interference indication that is transmitted to programmer 24 and/or generate an alert to notify patient 12 that neurostimulation therapy has been suspended.

The techniques described in this disclosure, including those attributed to IMD 16, programmer 24, or various constituent components, may be implemented, at least in part, in hardware, software, firmware or any combination thereof. For example, various aspects of the techniques as exemplarily shown and described in flow diagrams may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 100 of IMD 16 and/or processor 130 of programmer 24, any one or more parts of the techniques described herein may be implemented by a processor of IMD 16, programmer 24 or another computing device, alone or in combination with IMD 16 or programmer 24.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Figure 13:
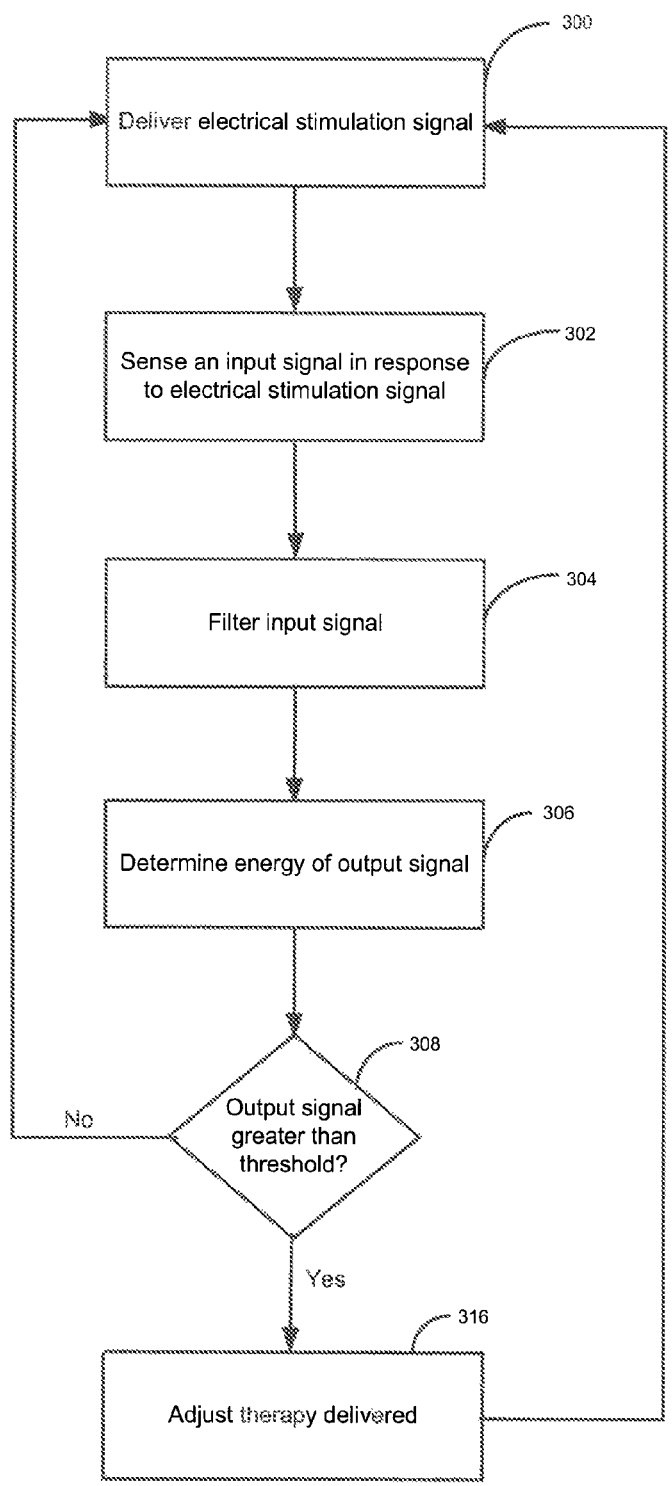
FIGS. 13-14 are flow diagrams of exemplary techniques for detection, elimination and/or prevention of laryngeal activation during vagal stimulation.
Figure 14:
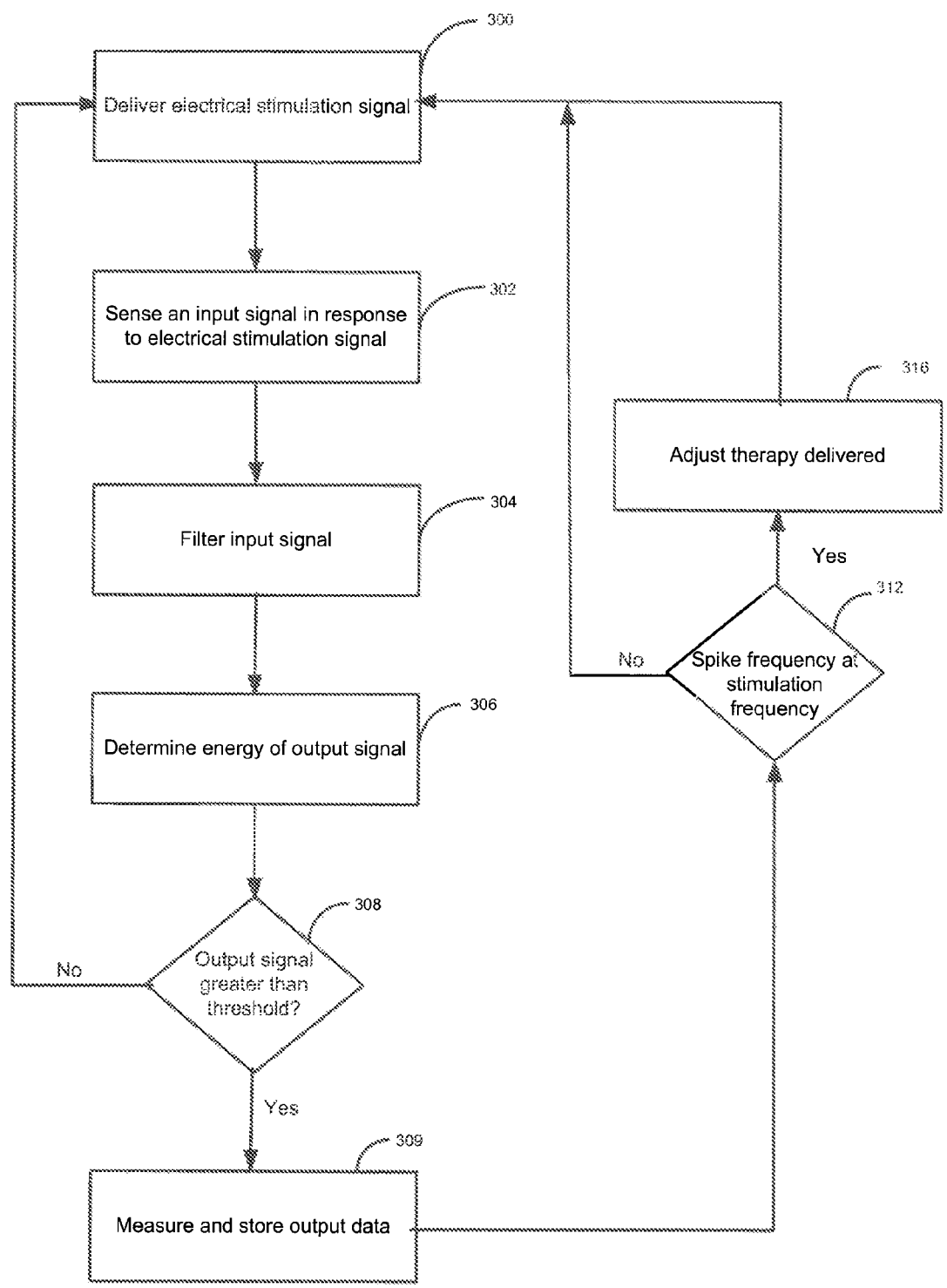

FIGS. 13-14 are flow diagrams of exemplary techniques to treat cardiac conditions such as heart failure through detection and control of laryngeal muscle activation, which, in turn, can lead to control of vagal stimulation. The techniques described herein can allow for maximum delivery of vagal stimulation while preventing or terminating laryngeal activation.

FIG. 13 is a flow diagram of computer instructions stored in memory (e.g. RAM) to detect laryngeal activation and then adjust the delivery of neurostimulation therapy to patient 12 in order to terminate or avoid laryngeal activation. In one or more embodiments, electrodes of neurostimulation lead 28 (FIG. 4) are used to deliver electrical stimulation signal(s) to patient 12 (block 300) from IMD 16. In particular, signal generator 116 of neurostimulation module 106 can generate an electrical stimulation signal to target tissue site 40 (FIG. 1) via one or more of electrodes 80-83 of lead 28. In some examples, the stimulation signal is configured to provide cardiac and/or neurostimulation therapy to patient 12. The stimulation signal may comprise, for example, a pulse waveform having a frequency of about 25 Hz and an amplitude of about 3 V. In another embodiment, the stimulation signal may comprise, for example, a pulse waveform having a frequency in a range of about 10 Hz to about 100 Hz and an amplitude of about 0.5 V to about 10 V.

After the electrical stimulation signal is delivered to patient 12, there are numerous ways to sense (302) the patient's physiologic response to the stimulation signal. Exemplary sensing elements can include an acoustic sensor, a pressure sensor, an accelerometer, a piezoelectric sensor and/or a strain gauge device. The piezoelectric sensor can measure sounds and collect signals in the range of a few millivolts, anywhere from a fraction of a millivolt up to 16 mV. Additionally, the piezoelectric sensor can convert the "force" of the vibration into a voltage.

Various types of accelerometers can also be used such as a rate response accelerometer or a heart sounds sensor. The heart sound sensor can be used to detect heart sounds to record or store signals for detecting laryngeal activation. An example of such a configuration may be seen with respect to U.S. patent application Ser. No. 12/495,204, entitled "HEART SOUND SENSING TO REDUCE INAPPROPRIATE TACHYARRHYTHMIA THERAPY" filed Jun. 30, 2009, and assigned to the assignee of the present invention, the disclosure of which is incorporated by reference in its entirety herein.

A patient's physiologic response, referred to as an input signal, can be sensed through a sensor, as described herein. In one or more embodiments, sensing module 118 (FIG. 4) of neurostimulation therapy module 106 may sense an electrical nerve signal, e.g., via a subset of electrodes 80-83 of lead 28. Nerve capture module 122 (FIG. 4) of IMD 16 may analyze the electrical nerve signal (202) to determine whether the delivery of the stimulation signal resulted in a physiological response (204). That is, nerve capture module 122 may analyze the electrical nerve signal to determine if the stimulation signal captured the nerve (e.g., the laryngeal nerve). Another way in which to sense a patient's physiologic response to the stimulation signal is through use of sensing module 114 of cardiac therapy module 104. In other examples, nerve capture module 122 also analyzes an electrical signal that is indicative of other physiological responses, such as muscle movement, to the delivery of the stimulation signal, as previously described. Nerve capture module 122 may analyze the electrical nerve signal to determine whether the nerve was captured by, for example, comparing an amplitude of the electrical nerve signal to a predetermined threshold amplitude value stored in memory 102 (FIG. 4) of IMD 16.

In particular, nerve capture module 122 may analyze a portion of the electrical nerve signal that corresponds to a time interval following delivery of the stimulation signal by neurostimulation therapy module 106. In one or more embodiments, the nerve capture module 122 can determine the energy level of the electrical nerve signal that corresponds to a time interval (e.g. time T1) following delivery of the stimulation signal by neurostimulation therapy module 106. If nerve capture module 122 detects a physiological response to the stimulation signal, processor 100 may determine that the energy level of the output signal is greater than a predetermined threshold level which is indicative of laryngeal activation for a patient. In contrast, if the energy level of the output signal is equal or less than a predetermined threshold level which means there is no laryngeal activation. The predetermined threshold level may be determined or customized for each patient by a doctor delivering electrical stimulation to a certain location in a patient until laryngeal activation is determined to have occurred. Alternatively, a doctor may determine the amount and/or location for delivering electrical stimulation that causes an average patient to experience laryngeal activation.

After the input signal has been sensed, the input signal passes through a filter (block 304) to remove noise. The filter can be bandpass centered at a laryngeal/vagal stimulation frequency. The laryngeal/vagal stimulation frequency, which is the predetermined threshold level, can be predetermined by a physician intentionally activating the larynx through electrical stimulation of tissue near the larynx. After the physician has determined the laryngeal/vagal stimulation frequency, the laryngeal/vagal stimulation frequency is stored into memory of the IMD. Optionally, the physician can also store into memory the approximate distance from the electrode delivering electrical stimulation to the target tissue. In one or more embodiments, a matched filter can also be used as a template of the laryngeal vibration output signal in order to detect laryngeal activation.

The energy of the filtered output signal is then determined (block 306). There are numerous ways in which to determine the energy level of the filtered output signal. For example, one method may involve classical signal detection in which the energy of the output is squared and then integrated. If the energy level of the filtered output signal is greater at block 308 than the energy level of the threshold signal for laryngeal activation, then laryngeal vibration has been detected. As previously mentioned, laryngeal/vagal stimulation frequency is stored in memory and serves as a threshold signal for laryngeal/vagal stimulation. At block 316, the electric stimulation is automatically adjusted during vagal stimulation in an ambulatory setting so as to achieve maximum vagal stimulation without larynx activation. Adjustment of electrical therapy can involve decreasing, or ceasing delivery of electrical stimuli. Alternatively, the electrical stimulation parameters can be adjusted. Electrical stimuli can be adjusted, for example, by adjusting the amplitude, frequency, duration, and/or duty cycle of a current (or voltage) for an electrical signal. Additionally, adjustment of electrical stimulation is automatically performed by the IMD on a predetermined incremental basis.

If the energy level of the filtered output signal is equal to or less than the energy level of the threshold signal for laryngeal activation, then no laryngeal vibration has been detected. The output signal energy is proportional to the voltage of an electrical signal. Typically, the electrical signal energy is a function of voltage-squared and the duration of the signal.

Thereafter, the control module 106 continues to deliver electrical stimulation signals at block 300. Optionally, a laryngeal vibration indicator signal is generated from the processor. The laryngeal vibration indicator signal can also be sent to an output device such as a Medtronic 2090 Programmer commercially available from Medtronic located in Minneapolis, Minn. or a hand held device for a user. The output device can be used by a clinician performing a medical procedure through a Medtronic 2090 Programmer.

FIG. 14 is yet another flow diagram to detect laryngeal activation and then adjust delivery of neurostimulation therapy to patient 12 based on detection of the laryngeal activation. FIG. 14 is the same as FIG. 13 except for the addition of blocks 309 and 312. At block 312, output data (e.g. time between peaks such as laryngeal peaks) is stored in memory. Lack of laryngeal peaks can indicate lack or loss of capture a response such if the medical electrical lead has moved out of its position. At block 312, a determination is made as to whether a spike frequency is generated at an electrical stimulation frequency. If the spike frequency is at the stimulation frequency, then the electrical therapy is adjusted at block 316 and then delivered at block 300. If the spike frequency is not at the stimulation frequency, then control of flow diagram is switched to block 300.

Processor 100 may control neurostimulation therapy module 106 to withhold the delivery of neurostimulation to patient 12 (206). Loss of nerve capture may indicate that lead 28 has migrated from the target tissue site 40. Because there is a possibility that lead 28 may have migrated to a position where neurostimulation therapy may be coupled to heart 14, IMD 16 may withhold delivery of neurostimulation therapy.

In one or more other embodiments, a physician performing surgery on a patient can cause electrical stimulation to be delivered, through one or more lead electrodes, proximate to nerve tissue. A response from the nerve can be used as an input signal to a processor located in an implantable medical device or, alternatively, a processor external to a patient. One such external processor is a nerve integrity monitor such as the Xomed NIM-2 XL commercially available from Medtronic located in Fridley, Minn. The nerve response, sensed through a medical electrical lead, can be analyzed through a processor. The NIM monitor is also configured to allow a user to periodically stimulate one or more nerves of the neck during ear, nose, and throat (ENT) surgery. By observing a response to electrical stimulation, the physician can determine whether a nerve has been inadvertently severed during a surgical procedure. The processor generally records nerve response amplitudes in the range of about 5 uV to about 10 mV. Typically, a nerve response of 1 mV is expected to occur.

Another embodiment for the "input signal" to analyze to determine a larynx response is a piezoelectric, either embedded in the device itself, or embedded in a lead proximal to the point of stimulation. IMD-based piezoelectric sensor are very sensitive to intra-body vibrations such as those from the larynx. For example, a piezoelectric sensor such as a "Patient Alert" speaker, can be used. Embedding a similar piezoelectric sensor or accelerometer at a distal end of a medical electrical lead proximal to the site of stimulation would be even more sensitive to vibrations in the larnyx, since it would be much closer to the larynx than would be the IMD. The piezoelectric sensor could be inserted into a polymeric sleeve on the outer surface of the lead body at the distal end of the lead.

The present disclosure can be implemented in two separate IMDs in which one device can communicate back-and-forth with the other device. Alternatively, a sound sensor (either piezoelectric or accelerometer) can be integrated with the neuro IMD. In the latter case, no cardiac IMD would be required.

While the invention has been described in its presently preferred form, it will be understood that the invention is capable of modification without departing from the spirit of the invention as set forth in the appended claims.

The invention claimed is:

1. A system of detecting displacement of an implanted neurological lead having an electrode for delivering electrical stimuli and sensing, the system comprising:
   means for delivering electrical stimulation through the neurological lead to laryngeal tissue;
   means for sensing laryngeal activity to produce an electromyogram (EMG) waveform;

means for storing the EMG waveform sensed at the time of implantation as a baseline pattern;
means for sensing laryngeal activity to produce an EMG waveform at a time subsequent to implantation;
means for storing the EMG waveform sensed at the time subsequent to implantation as a subsequent pattern;
means for comparing the baseline pattern and the subsequent pattern;
means for determining whether laryngeal activity decreased in the subsequent pattern from the baseline pattern; and
means for decreasing electrical stimulation delivered through the neurological lead in response to determining decreased laryngeal activity.

2. The system of claim 1 further comprising:
means for determining that the subsequent pattern lacks laryngeal activity; and
means for suspending electrical stimulation in response to determining that the subsequent pattern lacks laryngeal activity.

3. The system of claim 1 wherein the means for sensing laryngeal activity with the electrode to produce an EMG occurs at time of implantation of the lead.

4. The system of claim 1 wherein the means for determining whether laryngeal activity decreased in the subsequent pattern from the baseline pattern is based upon at least one of an amplitude and frequency associated with the baseline pattern and at least one of an amplitude and a frequency associated with the subsequent pattern.

5. The system of claim 3 wherein the frequency associated with the subsequent pattern is lower than the frequency for the baseline pattern.

6. The system of claim 1 wherein means for sensing laryngeal activity is through one of the electrode of the lead, an acoustic sensor, a pressure sensor, an accelerometer, and a piezoelectric sensor.

7. The system of claim 1 further comprising a cardiac lead disposed near cardiac tissue to deliver cardiac rhythm therapy.

8. The system of claim 1, wherein the means for delivering cardiac rhythm therapy and the means for delivering an electrical signal are enclosed within a common outer housing of an implantable medical device.

9. The system of claim 1 further comprising a first implantable medical device (IMD) comprising a first outer housing enclosing the means for delivering cardiac rhythm therapy and a second IMD comprising a second outer housing enclosing the means for delivering an electrical signal, wherein the first and second outer housings are physically separate from each other and separately implantable within the patient.

10. The system of claim 1, wherein the means for controlling controls the means for delivering the electrical signal to selectively deliver neurostimulation to the patient based on the detected laryngeal activity by at least controlling the means for delivering the electrical signal to deliver neurostimulation to the patient via the electrode of the lead if the physiological response is detected and controlling the means for delivering the electrical signal to withhold the delivery neurostimulation to the patient via the electrodes of the lead if the laryngeal activity is not detected.

11. A system of detecting displacement of an implanted neurological lead having an electrode for delivering electrical stimuli and sensing, the system comprising:
means for delivering electrical stimulation through the neurological lead to laryngeal tissue;
means for sensing laryngeal activity to produce an electrocardiogram (ECG) waveform;
means for storing the ECG waveform sensed at the time of implantation as a baseline pattern;
means for sensing laryngeal activity to produce an ECG waveform at a time subsequent to implantation;
means for storing the ECG waveform sensed at the time subsequent to implantation as a subsequent pattern;
means for comparing the baseline pattern and the subsequent pattern;
means for determining whether laryngeal activity decreased in the subsequent pattern from the baseline pattern; and
means for decreasing electrical stimulation delivered through the neurological lead in response to determining decreased laryngeal activity.

12. The system of claim 11 further comprising:
means for determining that the subsequent pattern lacks laryngeal activity; and
means for suspending electrical stimulation in response to determining that the subsequent pattern lacks laryngeal activity.

13. The system of claim 11 wherein the means for sensing laryngeal activity with an electrode from a cardiac lead to produce an electrocardiogram (ECG).

14. The system of claim 11 wherein the means for determining whether laryngeal activity decreased in the subsequent pattern from the baseline pattern is based upon a frequency associated with the baseline pattern and a frequency is associated with the subsequent pattern.

15. The system of claim 13 wherein the frequency associated with the subsequent pattern is lower than the frequency for the baseline pattern.

16. The system of claim 11 wherein the means for determining whether laryngeal activity decreased in the subsequent pattern from the baseline pattern is based upon an amplitude associated with the baseline pattern and an amplitude is associated with the subsequent pattern.

17. The system of claim 13 wherein the amplitude associated with the subsequent pattern is lower than the amplitude for the baseline pattern.

* * * * *